(12) United States Patent
Schrimpf et al.

(10) Patent No.: US 7,994,223 B2
(45) Date of Patent: Aug. 9, 2011

(54) AMIDE DERIVATIVES AS POSITIVE ALLOSTERIC MODULATORS AND METHODS OF USE THEREOF

(75) Inventors: Michael R. Schrimpf, Grayslake, IL (US); Kathleen H. Mortell, Chicago, IL (US); Diana L. Nersesian, Gurnee, IL (US); Chih-Hung Lee, Vernon Hills, IL (US); Bruce Clapham, Lindenhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/841,547

(22) Filed: Jul. 22, 2010

(65) Prior Publication Data

US 2010/0286109 A1 Nov. 11, 2010

Related U.S. Application Data

(62) Division of application No. 12/412,110, filed on Mar. 26, 2009, now Pat. No. 7,786,171.

(60) Provisional application No. 61/042,323, filed on Apr. 4, 2008.

(51) Int. Cl.
*A61K 31/166* (2006.01)
(52) U.S. Cl. .................................................... 514/618
(58) Field of Classification Search .................. None
See application file for complete search history.

(56) References Cited

U.S. PATENT DOCUMENTS

| 6,057,371 A | 5/2000 | Glennon |
| 7,160,876 B2 | 1/2007 | Ji et al. |
| 2004/0220247 A1 | 11/2004 | Keitz et al. |
| 2005/0065178 A1 | 3/2005 | Basha et al. |
| 2005/0137204 A1 | 6/2005 | Ji et al. |
| 2005/0245531 A1 | 11/2005 | Ji et al. |

FOREIGN PATENT DOCUMENTS

| EP | 521365 A1 | 1/1993 |
| WO | WO0116097 A1 | 3/2001 |
| WO | WO2004029053 A1 | 4/2004 |
| WO | WO2007105814 A1 | 9/2007 |
| WO | WO2008039489 A2 | 4/2008 |

OTHER PUBLICATIONS

"Pain," Merck Manuals Online Medical Library: Home Edition. Accessed Mar. 24, 2009. <http://www.merck.com/mmhe/sec06/ch078/ch078a.html>.*
Stillman, Mark. "Clinical approach to patients with neuropathic pain." Cleveland Clinic Journal of Medicine, 73 (8), pp. 726-730, 733-739.*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Wolff et al. Burger's Medicinal Chemistry and Drug Discovery. 5th ed. vol. 1: Principles and Practice. pp. 975-977.*
Acklin, P. et al. , "5-aminomethylquinoxaline-2,3-diones, Part III: Arylamide derivatives as highly potent and selective glycine-site NMDA receptor antagonists," Bioorganic & Medicinal Chemistry Letters, vol. 8 No. 5, pp. 493-498 , 1998.
Adler et al., "Schizophrenia, sensory gating, and nicotinic receptors," Schizophrenia Bulletin , vol. 24 (2), pp. 189-202, 1998.
Adler, L. E. et al., Biol. Psychiatry, vol. 21, pp. 787-798, 1986.
Albuquerque et al., "Modulation of nicotinic receptor activity in the central nervous system: a novel approach to the treatment of Alzheimer disease," Alzheimer Dis. Assoc. Disord, vol. 15 Suppl 1, pp. s19-s25, 2001.
Alkondon, et al., "The nicotinic acetylcholine receptor subtypes and their function in the hippocampus and cerebral cortex", Prog. Brain Res., 2004, 145, 109-120.
Balbani A., et al., "Recent developments for smoking cessation and treatment of nicotine dependence", Expert. Opin. Ther. Pat., 2007, 17 (3), 287-297.
Bitner et al., "Broad-spectrum efficacy across cognitive domains by alpha7 nicotinic acetylcholine receptor agonism correlates with activation of ERK1/2 and CREB phosphorylation pathways," J. Neurosci., 2007, vol. 27 (39), pp. 10578-10587.
Bowen, M.D., et al., Mol. Neuropharmacol., vol. 3, pp. 117-126, 1993.
Briggs, C.A. et al.,"Human a 7 Nicotinic Acetylcholine Receptor Responses to Novel Ligands"Neuropharmacology, vol. 34, pp. 583-590, 1995.
Briggs, C.A., et al., "Activation and inhibition of the human alpha7 nicotinic acetylcholine receptor by agonists," Neuropharmacology, vol. 37, pp. 1095-1102 , 1998.
Broad L. M., et al., "Selective alpha7 nicotinic acetylcholine receptor ligands for the treatment of neuropsychiatric diseases", Drugs of the Future, 2007, 32 (2), 161-170.
Bunnelle, W.H., et al., Exp. Opin. Ther. Patents, vol. 13(7), pp. 1003-1021, 2003.
Connolly, P.M., et al. Brain Res, vol. 992 (1) , pp. 85-95, 2003.
European Search Report dated Nov. 25, 2009 for EP09156652.
International Search Report for PCT/US2009/038474 dated Nov. 24, 2009.
Cordero-Erausquin et al. , "Tonic nicotinic modulation of serotoninergic transmission in the spinal cord," PNAS, vol. 98 (5), pp. 2803-2807, 2001.
Couturier S., et al., "A Neuronal Nicotinic Acetylcholine Receptor Subunit (alpha7) Is Developmentally Regulated and forms a Homo-Oligomeric Channel Blocked by alpha-BTX", Neuron, 1990, 5, 847-856.

(Continued)

*Primary Examiner* — Rebecca Anderson
*Assistant Examiner* — Alicia L Otton
(74) *Attorney, Agent, or Firm* — Nancy J. Gettel; Antonia M. Holland

(57) ABSTRACT

The invention relates to novel amide derivatives that are positive allosteric modulators of neuronal nicotinic receptors, compositions comprising the same, processes for preparing such compounds, and methods for using such compounds and compositions.

5 Claims, 3 Drawing Sheets

OTHER PUBLICATIONS

Dajas Bailador F., et al., "Nicotinic acetylcholine receptors and the regulation of neuronal signalling", Trends in Pharm. Sci., 2004, 25 (6), 317-324.

D'Andrea et al., "Targeting the alpha 7 nicotinic acetylcholine receptor to reduce amyloid accumulation in Alzheimer's disease pyramidal neurons," Curr. Pharm. Des., vol. 12, pp. 677-684, 2006.

De Luca V., et al., "Regulation of alpha7-nicotinic receptor subunit and alpha7-like gene expression in the prefrontal cortex of patients with bipolar disorder and schizophrenia", Acta Psychiatr. Scand., 2006, 114, 211-215.

Decker M. W., et al., "The therapeutic potential of nicotinic acetylcholine receptor agonists for pain control", Expert Opin. Investig. Drugs, 2001, 10 (10), 1819-1830.

Dunlop, J. et al., "In vitro screening strategies for nicotinic receptor ligands," Biochemical Pharmacology, vol. 74 No. 8, pp. 1172-1181, 2007.

Ettmayer, Peter "Lessons Learned from Marketed and Investigational Prodrugs", Medicinal Chemistry, 2004, vol. 47—Issue 10, 2393-2404.

Faghih, R. et al., "Advances in the Discovery of Novel Positive Allosteric Modulators of the alpha7 Nicotinic Acetylcholine Receptor," Recent patent on CNS Drug Disc., vol. 2 (2) , pp. 99-106, 2007.

Friedman et al., "A double blind placebo controlled trial of donepezil adjunctive treatment to risperidone for the cognitive impairment of schizophrenia," Biol. Psychiatry, vol. 51, pp. 349-357, 2002.

Furniss B. S. et al, "Practical Organic Chemistry", 5th Ed., Longman Scientific & Technical & John Wiley & Sons, Inc., Table of Contents, 1989.

Ganapathy, M.E., et al., J. Pharmacol. Exp. Ther., vol. 289, pp. 251-260, 1999.

Gotti Clementi,, "Neuronal nicotinic receptors: from structure to pathology", Progress in Neurobiology, 2004, 74, 363-396.

Gotti, et al., "Brain neuronal nicotinic receptors as new targets for drug discovery," Curr. Pharm. Des. , vol. 12, pp. 407-428, 2006.

Greene T.W., et al., "Protection for the Amino group," Protective Groups in Organic Synthesis, 1999, Edition 3, John Wiley & Sons, 494-653.

Gundish D.,, "Nicotinic acetylcholine receptor ligands as potential therapeutics", Expert Opin. Ther. Patents, 2005, 15 (9), 1221-1239.

Gurwitz D.,, "The therapeutic potential of nicotine and nicotinic agonists for weight control", Exp. Opin. Invest. Drugs, 1999, 8 (6), 747-760.

Hevers, W. Luddens, H., "The Diversity of GABA, Receptors," Molec.. Neurobiol., vol. 18, pp. 35-86, 1998.

Higuchi T., et al., "Pro-drugs as Novel Delivery Systems," Bioreversible Carriers in Drug Design, 1987, 14, American Pharmaceutical Association and Pergamon Press.

Hogg, et al.,, "Nicotinic acetylcholine receptors: From structure to brain function", Rev. Physiol Biochem. Pharmacol., 2003, 147, 1-46.

Holladay et al., "Neuronal Nicotinic Acetylcholine Receptors as Targets for Drug Discovery," J. Med. Chem., vol. 40 (26), pp. 4169-4194, 1997.

Hunter et al., "A novel nicotinic against facilitates induction of long-term potentiation in the rat hippocampus," Neurosci. Lett., vol. 168, pp. 130-134, 1994.

Hurst et al., "A novel positive allosteric modulator of the alpha7 neuronal nicotinic acetylcholine receptor: in vitro and in vivo characterization," J. Neurosci. , vol. 25 (17), pp. 4396-4405, 2005.

IUPAC Commission on Nomenclature of Organic Chemistry: Rules for the Nomenclature of Organic Chemistry Section E: Stereochemistry, Pure Appl Chem, 1976, 45, 11-30.

Jonnala, et al. "Relationship between the increased cell surface .alpha.7 nicotinic receptor expression and neuroprotection induced by several nicotinic receptor agonists", Journal of Neuroscience Research, 2001, 66, 565-572.

Keller, et al. "Performance of alpha7 nicotinic receptor null mutants is impaired in appetitive learning measured in a signaled nose poke task", Behav. Brain Res., 2005, 162, 143-152.

Kihara, et al., "alpha.7 Nicotinic receptor transduces signals to phosphatidylinositol 3-kinase to block A .beta.-amyloid-induced neurotoxicity", Journal of Biological Chemistry, 2001, 276 (17), 13541-13546.

Korolkova, A., "Essentials of Medicinal Chemistry," John Wiley-Interscience Publications, 97-118, 1988.

Leonard et al., "Smoking and schizophrenia: abnormal nicotinic receptor expression," European Journal of Pharmacology, vol. 393, pp. 237-242, 2000.

Levin E. D.,, "Nicotinic Receptor Subtypes and Cognitive Function", J Neurobiol, 2002, 53, 633-640.

Liu, et al., "alpha.-Amyloid peptide blocks the response of .alpha.7-containing nicotinic receptors on hippocampal neurons", PNAS, 2001, 98 (8), 4734-4739.

Martin, L.F. et al. , "Alpha-7 nicotinic receptor agaonists potential new candidates for the treatment of schizophrenia ," Pschopharm., vol. 174, pp. 54-64, 2004.

Paterson, D., et al. "Neuronal nicotinic receptors in the human brain", Progress in Neurobiology, 2000, 61, 75-111.

Pavlov, V. A., et al., Biochem. Soc. Trans., vol. 34 (6), pp. 1037, 2006.

Pichat, R, et al., "SSR180711A, a novel selective alpha-7 nicotinic receptor partial agonist III Effects in models predictive of therapeutic activity on cognitive symptoms of schizophrenia," Soc. for Neurosci., 2004.

Prescott et al., "Lipid Vesicles as Carriers for Introducing Biologically Active Materials into Cells," Methods in Cell Biology, 1976, Academic Press, 33-71.

Roche E., "Bioreversible Carriers in Drug Design, American Pharmaceutical Association and Pergamon Press Table of Contents," 1987.

Romanelli, M.N. et al., "The quest for the treatment of cognitive impairment: alpha7 nicotinic and alpha5 GABAA receptor modulators," Expert Opin. Ther Patents, vol. 17 (11), pp. 1365-1377, 2007.

Rowley et al., "Current and novel approaches to the drug treatment of schizophrenia," Journal of Medicinal Chemistry, vol. 44 (4), pp. 477-501, 2001.

Shimohama, et al., "Nicotinic .alpha.7 receptors protect against glutamate neurotoxicity and neuronal ischemic damage", Brain Research, 1998, 779, 359-363.

Shirayama, Y., et al., Eur. J. Pharmacol., vol. 237, pp. 117-126 , 1993.

Stella et al., Prodrugs as therapeutics, 2004, 14 (3), 277-280.

Stevens et al., "Selective a7-nicotinic agonists normalize inhibition of auditory response in DBA mice," Psychopharmacology, vol. 136, pp. 320-327, 1998.

Stevens, K.E., et al., Psychopharmacology, vol. 119, pp. 163-170 , 1995.

Testa, Bernard "Prodrug Research: futile or fertile?", Biochemical Pharmacology, 2004, vol. 68, 2097-2106.

Trumbull, J.D., et al., "High Throughput Electrophysiology Using a Fully Automated, Multiplexed Recording System", Receptors Channels, vol. 9, 19-28, 2003.

Van Kampen M., et al., "AR-R 17779 improves social recognition in rate by activation of nicotinic alpha7 receptors," Psychopharmacology, vol. 172, pp. 375-383, 2004.

Vincler M.,, "Neuronal nicotinic receptors as targets for novel analgesics", Expert Opin. Investig. Drugs, 2005, 14 (10), 1191-1198.

Vincler M.,, "Targeting the alpha9alpha10 nicotinic acetylcholine receptor to treat severe pain", Expert Opin. Ther. Targets 2007, 11 (7), 891-897.

Wang et al., "Nicotinic acetylcholine receptor .alpha.7 subunit is an essential regulator of inflammation," Nature, vol. 421, pp. 384-388, 2003.

Wolff, Mandred E.,, "Burger's Medicinal Chemistry and Drug Discovery," Principles and Practice, 1995, 975-977, 5th Ed,vol. 1, John Wiley & Sons.

* cited by examiner

Effect of Example 20 in Formalin (Phase 2) Model of Nociceptive Pain

Effect of Example 20 Upon Normalization of Sensory Gating Deficit in DBA/2 Mice
(N40 Gating)

AMIDE DERIVATIVES AS POSITIVE ALLOSTERIC MODULATORS AND METHODS OF USE THEREOF

This application is a divisional application of U.S. patent application Ser. No.12/412,110,filed on Mar. 26, 2009, now U.S. Pat. No. 7,786,171, which in turn claims the benefit of U.S.Provisional Patent Application No. 61/042,323, filed Apr. 4, 2008, both of which are incorporated herein by reference.

TECHNICAL FIELD

The invention relates to novel amide derivatives that are positive allosteric modulators of neuronal nicotinic receptors, compositions comprising the same, and methods for using such compounds and compositions.

DESCRIPTION OF RELATED TECHNOLOGY

Nicotinic acetylcholine receptors (nAChRs), belonging to the superfamily of ligand gated ion channels (LGIC), gate the flow of cations, controlled by acetylcholine (ACh). The nAChRs can be divided into nicotinic receptors of the muscular junction and neuronal nicotinic receptors (NNRs). NNRs are widely distributed throughout the central nervous system (CNS) and the peripheral nervous system (PNS). NNRs play an important role in regulating CNS function and the release of many neurotransmitters, for example, ACh, norepinephrine, dopamine, serotonin, and GABA, among others, resulting in a wide range of physiological effects.

nAChRs are typically pentameric assemblies composed of protein subunits surrounding a central ion channel. Sixteen subunits have been reported to date, which are identified as $\alpha 2$-$\alpha 10$, $\beta 1$-$\beta 4$, $\gamma$, $\delta$, and $\epsilon$. Of these subunits, $\alpha 2$ through $\alpha 7$ and $\beta 2$ through $\beta 4$, are highly expressed in the mammalian brain. Other functionally distinct nAChR complexes also exist, for example five $\alpha 7$ subunits can form a receptor as a homomeric functional pentamer or combinations of different subunits can complex together as in the case of $\alpha 4\beta 2$ and $\alpha 3\beta 4$ receptors (see for example, Paterson, D., et al., *Prog. Neurobiol.* 2000, 61: 75-111; Hogg, R. C., et al., *Rev. Physiol., Biochem. Pharmacol.*, 2003, 147: 1-46; Gotti, C., et al., *Prog. Neurobiol.*, 2004, 74: 363-396).

The homomeric $\alpha 7$ receptor is one of the most abundant nicotinic receptors, along with $\alpha 4\beta 2$ receptors, in the human brain, wherein it is expressed in the hippocampus, cortex, thalamic nuclei, ventral tegmental area and substantia nigra (see for example, Broad, L. M., et al., *Drugs of the Future*, 2007, 32(2): 161-170).

The role of $\alpha 7$ NNRs in neuronal signaling in the CNS also has been actively investigated (see for example, Couturier, S., et al., *Neuron*, 1990, 5: 847-56). The $\alpha 7$ NNRs have been demonstrated to regulate interneuron excitability, modulate the release of excitatory and inhibitory neurotransmitters, and lead to neuroprotective effects in experimental in vitro models of cellular damage (see for example, Alkondon, M., et al., *Prog. Brain Res.*, 2004, 145: 109-20).

Biophysical studies have shown that ion channels comprised of $\alpha 7$ subunits, when expressed in heterologous expression systems, activate and desensitize rapidly, and furthermore, exhibit relatively higher calcium permeability compared to other NNR combinations (see for example, Dajas-Bailador, F., et al, *Trends Pharmacol. Sci.*, 2004, 25: 317-24).

The NNRs, in general, are involved in various cognitive functions, such as learning, memory, attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain, TNF-$\alpha$ release and inflammation, and tobacco dependence (see for example, Keller, J. J., et al., *Behav. Brain Res.*, 2005, 162: 143-52; Gundish, D., *Expert Opin. Ther. Patents*, 2005, 15 (9): 1221-1239; De Luca, V., et al., *Acta Psychiatr. Scand.*, 2006, 114: 211-5; Wong, H. et al *Nature*, 2003, 421, 384; Pavlov, V. A. et al., *Biochem. Soc. Trans.*, 2006, 34(6), 1037).

More particularly, $\alpha 7$ NNRs have been linked to conditions and disorders related to attention deficit disorder, ADHD, AD, mild cognitive impairment (MCI), senile dementia, dementia associated with Lewy bodies, dementia associated with Down's syndrome, AIDS dementia, Pick's disease, as well as cognitive deficits associated with schizophrenia (see for example, Martin, L. F., et al., *Psychopharmacology* (Berl), 2004, 174: 54-64; Romanelli, M. N., et al., *Exp. Opin. Ther. Patents*, 2007, 17 (11): 1365-1377). The $\alpha 7$ NNRs have also been reported to slow disease progression in AD (D'Andrea, M. R., et al., *Curr. Pharm. Des.*, 2006, 12: 677-84).

Accordingly, modulating the activity of $\alpha 7$ NNRs demonstrates promising potential to prevent or treat a variety of diseases indicated above, such as AD, other dementias, schizophrenia and neurodegeneration, with an underlying pathology that involves cognitive function including, for example, aspects of learning, memory, and attention (see for example, Gotti, C., et al., *Curr. Pharm. Des.*, 2006, 12: 407-428).

NNR ligands have been also implicated in smoking cessation, weight control and as potential analgesics (see for example, Balbani, A. P. S., et al., *Exp. Opin. Ther. Patents*, 2003, 13 (7): 287-297; Gurwitz, D., *Exp. Opin. Invest. Drugs*, 1999, 8(6): 747-760; Vincler, M., *Exp. Opin. Invest. Drugs*, 2005, 14 (10): 1191-1198; Bunnelle, W. H., et al., *Exp. Opin. Ther. Patents*, 2003, 13 (7): 1003-1021; Decker, M. W., et al., *Exp. Opin. Invest. Drugs*, 2001, 10 (10): 1819-1830; Vincler, M., et al., *Exp. Opin. Ther. Targets*, 2007, 11 (7): 891-897).

Nicotine is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems. Therefore, it is likely that subtype-selective nicotinic ligands may have the beneficial effects of nicotine without the undesired effects.

Examples of reported NNR ligands, such as PNU-282987 and SSR180711A, are $\alpha 7$ NNR agonists (see for example, Hajos, M., et al., *J. Pharmacol. Exp. Ther*, 2005, 312: 1213-22; Pichat, P., et al., *Society for Neuroscience Abstract*, 2004, number 583.3).

Another compound, AR-R17779, has been reported to improve performance of rats in social recognition, water mazes, or inhibitory avoidance models of cognitive domains (Van Kampen, M., et al., *Psychopharmacology* (Berl), 2004, 172: 375-83). AR-R17779 also reportedly facilitates the induction of hippocampal long-term potentiation (LTP) in a proposed cellular model for learning and memory in rats (Hunter, B. E., et al., *Neurosci. Lett.*, 1994, 168: 130-4). Compound A-582941, an $\alpha 7$ NNR agonist, has been shown to enhance cognitive performance associated with neurodegenerative diseases such as AD and schizophrenia (Bitner, R. S., et al., *J. Neuroscience*, 2007, 27(39): 10578-10587).

Despite the beneficial effects of NNR ligands, it remains uncertain whether chronic treatment with agonists affecting NNRs may provide suboptimal benefit due to sustained activation and desensitization of the NNR. In contrast to agonists, administering a positive allosteric modulator (PAM) can reinforce endogenous cholinergic transmission without directly simulating the target receptor (see for example, Albuquerque, E. X., et al., *Alzheimer Dis. Assoc. Disord.*, 2001, 15 Suppl 1: S19-25). Nicotinic PAMs could selectively modulate the activity of ACh at α7 NNRs. Accordingly, more recently, α7 NNR-selective PAMs have emerged (see for example, Faghih, R., et al., *Recent Patents on CNS Drug Discovery*, 2007, 2 (2): 99-106).

Consequently, it would be beneficial to target α7 NNR function by enhancing effects of the endogenous neurotransmitter acetylcholine via PAMs that can reinforce the endogenous cholinergic neurotransmission without directly activating α7 NNRs, like agonists. Indeed, PAMs for enhancing channel activity have been proven clinically successful for GABA$_A$ receptors where benzodiazepines, barbiturates, and neurosteroids behave as PAMs acting at distinct sites (see for example, Hevers, W., et al., *Mol. Neurobiol.*, 1998, 18: 35-86).

To date, only a few NNR PAMs are known, such as 5-hydroxyindole (5-HI), ivermectin, galantamine, bovine serum albumin, and SLURP-1, a peptide derived from acetylcholinesterase (AChE). Recently, genistein, a kinase inhibitor was reported to increase α7 responses, and PNU-120596, a urea derivative, was reported to increase the potency and maximal efficacy of ACh as well as improve auditory gating deficits induced by amphetamine in rats. Other NNR PAMs include derivatives of quinuclidine, indole, benzopyrazole, thiazole, and benzoisothiazoles (see for example, Hurst, R. S., et al., *J. Neurosci.*, 2005, 25: 4396-4405; Broad, L. M., et al., *Drugs of the Future*, 2007, 32(2):161-170; U.S. Pat. No. 7,160,876).

Accordingly, it would be beneficial to identify and provide new NNR PAMs and compositions for treating or preventing conditions associated with α7 NNRs. It would further be particularly beneficial if such compounds can provide improved efficacy of treatment while reducing adverse effects associated with compounds targeting neuronal nicotinic receptors by selectively modulating α7 NNRs.

Consequently, various embodiments of the present invention disclose novel amide derivatives that show α7 NNR PAM activity.

SUMMARY OF THE INVENTION

An embodiment relates to compounds of formula (I):

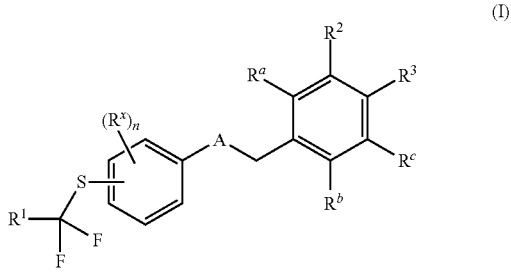

wherein,

A is —C(O)NH— or —NHC(O)—;

$R^a$, $R^b$, and $R^c$ are independently hydrogen, alkenyl, alkoxy, alkoxycarbonyl, alkyl, alkylcarbonyl, alkylsulfonyl, alkylthio, cyano, haloalkoxy, haloalkyl, or halogen;

$R^x$ at each occurrence is independently acyloxy, alkoxy, alkyl, haloalkyl, halogen, or hydroxy;

n is 0, 1, 2, 3, or 4;

$R^1$ is hydrogen or halogen;

$R^2$ and $R^3$ are independently hydrogen, alkenyl, alkoxy, alkoxycarbonyl, alkyl, alkylcarbonyl, alkylsulfonyl, alkylthio, cyano, haloalkoxy, haloalkyl, halogen or $NR^5R^6$, provided that at least one of $R^2$ or $R^3$ is $NR^5R^6$;

$R^5$ and $R^6$ are independently hydrogen, alkenyl, alkoxyalkyl, alkoxycarbonyl, alkyl, alkylcarbonyl, alkylsulfonyl, arylalkyl, cycloalkyl, cycloalkylalkyl, haloalkyl, heteroarylalkyl, heterocycle, or heterocyclealkyl; or $R^5$, $R^6$ and the nitrogen atom to which they are attached form an optionally substituted monocyclic heteroaryl or an optionally substituted monocyclic heterocycle;

or a pharmaceutically acceptable salt, ester, amide or prodrug thereof.

Another embodiment relates to a method of using compounds of formula (I) or pharmaceutically acceptable salts, esters, amides or prodrugs thereof.

Yet another embodiment is directed to a method of treating conditions and disorders that are regulated by the NNRs using compounds of formula (I) or therapeutically effective compositions of compounds of formula (I) or pharmaceutically acceptable salts, esters, amides or prodrugs thereof.

A further embodiment is directed to a method of treating a disorder or condition that is modulated by α7 nicotinic acetylcholine receptors in a patient in need of such treatment, comprising administering a therapeutically effective amount of a compound of formula (I) or pharmaceutically acceptable salts, esters, amides or prodrugs thereof.

Another embodiment relates to a method of assessing or diagnosing conditions or disorders related to α7 NNR activity comprising allowing isotope-labeled forms of compounds of formula (I) to interact with cells expressing endogenous α7 NNRs or cells expressing recombinant α7 NNRs and measuring the effects of such isotope-labeled forms of compounds on such cells.

Various embodiments also describe the use of NNR ligands, and particularly PAM compounds, to identify other useful target compounds for treating or preventing, or both, diseases or conditions associated with NNR function, in cell-based assays, for example in high-throughput format, using cells or tissues that express native α7 NNR receptors for the purpose of identifying novel α7 NNR agonists or PAMs of the α7 NNR.

DETAILED DESCRIPTION OF THE INVENTION

Definition of Terms

Figure 1:
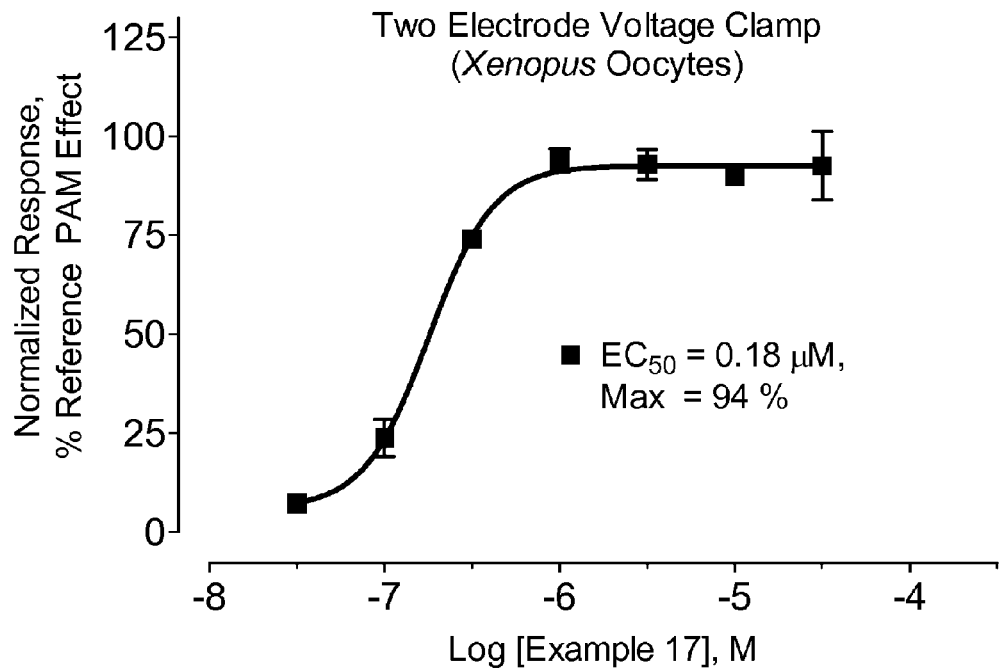
FIG. 1 is a graphical representation of a concentration response curve where submaximum ACh-evoked α7 current potentiation responses are measured in the presence of increasing concentrations of a PAM (Example 17) and normalized to the effect of a reference 10 μM PAM (N'-[(2Z)-3-(2,2-difluoro-1,3-benzodioxol-5-yl)-5-methyl-1,3-thiazol-2 (3H)-ylidene]-N,N-dimethylurea).

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

As used throughout this specification and the appended claims, the following terms have the following meanings.

The term "acetyl" means a —C(O)CH$_3$ group.

The term "acyl" means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" means an acyl group, as defined herein, appended to the parent molecular moiety through an oxygen atom. Representative examples of acyloxy include, but are not limited to, acetyloxy, propionyloxy, and isobutyryloxy.

The term "alkenyl" means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, hexyloxy and the like.

The term "alkoxyalkoxy" means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" means an alkoxy group, as defined herein, appended to the parent molecular moiety through a —C(=NH)— group, which also is defined as an imino group. Representative examples of alkoxyimino include, but are not limited to, imino(methoxy)methyl, ethoxy(imino)methyl and tert-butoxy(imino)methyl.

The term "alkoxysulfonyl" means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcycloalkyl" means an alkyl group, as defined herein, appended to the parent molecular moiety through a cycloalkyl group, as defined herein. Representative examples of alkylcycloalkyl include, but are not limited to, 4-ethylcyclohexyl, 3-methylcyclopentyl, and 2-isopropylcyclopropyl.

The term "alkylsulfonyl" means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" means an alkyl group, as defined herein, appended to the parent molecular moiety through a sulfur atom. Representative examples of alkylthio include, but are not limited, methylthio, ethylthio, tert-butylthio, and hexylthio.

The term "amino" refers to —NR$^{90}$R$^{91}$, wherein R$^{90}$ and R$^{91}$ are independently selected from hydrogen and alkyl, as defined herein. Representative examples of amino include, but are not limited to, amino, methylamino, ethylmethylamino, methylisopropylamino, dimethylamino, diisopropylamino, diethylamino, and the like.

The term "alkynyl" means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl" means phenyl, a bicyclic aryl, or a tricyclic aryl. The bicyclic aryl is naphthyl, a phenyl fused to a cycloalkyl, or a phenyl fused to a cycloalkenyl. The bicyclic aryl must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The aryl groups of this invention can be substituted with 1, 2, or 3 substituents independently selected from the group consisting of alkoxy, alkyl, aryloxy, carboxy, carboxyalkyl, cycloalkyl, cycloalkoxy, halogen, haloalkoxy, haloalkyl, halothioalkoxy, hydroxyl, mercapto, thioalkoxy, thiocycloalkoxy, and thioaryloxy.

The term "arylalkyl" means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "aryloxy" means an aryl group, as defined herein, appended to the parent molecular moiety through an oxygen atom. Representative examples of aryloxy include, but are not limited to, phenoxy and tolyloxy.

The term "carbonyl" means a —C(O)— group.

The term "carboxy" means a —CO$_2$H group.

The term "carboxyalkyl" means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" means a —CN group, attached to the parent molecular moiety through the carbon.

The term "cyanoalkyl" means a —CN group attached to the parent molecular moiety through an alkyl group. Representative examples of "cyanoalkyl" include, but are not limited to, 3-cyanopropyl, and 4-cyanobutyl.

The term "cycloalkoxy" means a cycloalkyl group, as defined herein, appended to the parent molecular moiety through an oxygen atom. Representative examples of cycloalkoxy include, but are not limited to, cyclohexyloxy and cyclopropoxy.

The term "cycloalkoxyalkyl" means a cycloalkoxy group, as defined herein, appended to the parent molecular moiety through an alkyl group, wherein alkyl is as defined herein. Representative examples of cycloalkoxyalkyl include, but are not limited to, cyclobutoxymethyl, cyclopentyloxymethyl, 2-(cyclopentyloxy)ethyl and cyclohexyloxymethyl.

The term "cycloalkyl" means a saturated cyclic hydrocarbon group containing from 3 to 10 carbons. Examples of cycloalkyl include cyclopropyl, cyclobutyl, cyclopentyl, cyclohexyl, cycloheptyl, and cyclooctyl.

The cycloalkyls are substituted with 0, 1, 2, 3, 4, 5, 6, 7, 8, or 9 substituents independently selected from the group consisting of acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, phenyl, oxo, —NR$^{98}$R$^{99}$, (NR$^{98}$R$^{99}$)carbonyl, —SO$_2$N(R$^{98}$)(R$^{99}$), —NR$^{98}$(C═O)NR$^{98}$R$^{99}$, —NR$^{98}$(C═O)Oalkyl, and —N(R$^{98}$)SO$_2$(R$^{99}$), wherein R$^{98}$ and R$^{99}$ each are each independently selected from acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, haloalkyl, halocycloalkyl, halocycloalkylalkyl, heteroaryl, heterocycle, hydrogen, formyl, hydroxy, and hydroxyalkyl.

The term "cycloalkylalkyl" means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl.

The term "fluoroalkoxy" means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, and 2,2,2-trifluoroethoxy.

The term "formyl" means a —C(O)H group.

The term "halo" or "halogen" means —Cl, —Br, —I or —F.

The term "haloalkoxy" means at least one halogen, as defined herein, appended to the parent molecular moiety through an alkoxy group, as defined herein. Representative examples of haloalkoxy include, but are not limited to, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, difluoromethyl, chloromethyl, 2-fluoroethyl, trifluoromethyl, 2,2,2-trifluoroethyl, pentafluoroethyl, and 2-chloro-3-fluoropentyl.

The term "halocycloalkyl" means at least one halogen, as defined herein, appended to the parent molecular moiety through a cycloalkyl group, as defined herein. Representative examples of halocycloalkyl include, but are not limited to, fluorocyclohexyl, bromocyclopropyl, and trans-2,3-dichlorocyclopentyl.

The term "halocycloalkylalkyl" means a halocycloalkyl group as defined herein, attached to the parent molecular moiety through an alkyl group. Representative examples of halocycloalkylalkyl include, but are not limited to, (4-fluorocyclohexyl)methyl, (2,2-difluorocyclobutyl)methyl and the like.

The term "halothioalkoxy" means at least one halogen, as defined herein, appended to the parent molecular moiety through a thioalkoxy group, as defined herein. Representative examples of halothioalkoxy include, but are not limited to, 2-chloroethylsulfane and trifluoromethylsulfane.

The term "heteroaryl" means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, 1H-pyrrolo[2,3-b]pyridinyl, quinolinyl, quinoxalinyl and thienopyridinyl.

The heteroaryl groups are optionally substituted with 1, 2, 3 or 4 substituents independently selected from the group consisting of aryloxy, alkenyl, alkoxy, alkoxycarbonyl, alkyl, alkylcarbonyl, alkylsulfonyl, alkylthio, alkynyl, amido, aryl, aryloxy, carboxy, carboxyalkyl, cyano, cyanoalkyl, cycloalkyl, cycloalkoxy, formyl, haloalkoxy, haloalkyl, halogen, halothioalkoxy, phenyl, chlorophenyl, thioalkoxy, thiocycloalkoxy, thioaryloxy, nitro, and —NR$^7$R$^8$, wherein R$^7$ and R$^8$ are independently acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, haloalkyl, halocycloalkyl, halocycloalkylalkyl, heteroaryl, heterocycle, hydrogen, formyl, hydroxy, or hydroxyalkyl.

The term "heteroarylalkyl" means a heteroaryl, as defined herein, appended to the parent molecular moiety through an alkyl group, as defined herein.

The term "heterocycle" or "heterocyclic" means a monocyclic heterocycle or a bicyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring contains zero, one, or two double bonds provided that the ring, when taken together with a substituent, does not tautomerize with a substituent to form an aromatic ring and one, two, three, or four heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, hexahydropyrrolo[3,4-b]pyrrol-1(2H)-yl, tetrahydro-1H-pyrrolo[3,4-b]pyridin-6(2H,7H,7aH)-yl, and 1,2,3,4-tetrahydroquinolinyl.

The heterocycles are substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cyanoalkyl, cycloalkyl, formyl, haloalkoxy, haloalkyl, halogen, hydroxy, hydroxyalkyl, mercapto, nitro, oxo, —NR$^{98}$R$^{99}$, (NR$^{98}$R$^{99}$)carbonyl, —SO$_2$N(R$^{98}$)(R$^{99}$), —NR$^{98}$(C═O)NR$^{98}$R$^{99}$, —NR$^{98}$(C═O)Oalkyl, and —N(R$^{98}$)SO$_2$(R$^{99}$), wherein R$^{98}$ and R$^{99}$ each are each independently acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, haloalkyl, halocycloalkyl, halocycloalkylalkyl, heteroaryl, heterocycle, hydrogen, formyl, hydroxy, or hydroxyalkyl.

The term "heterocyclealkyl" means a heterocycle, as defined herein, appended to the parent molecular moiety through an alkyl group, as defined herein. Representative examples of heterocyclealkyl include, but are not limited, (pyrrolidin-2-yl)methyl, 2-(morpholin-4-yl)ethyl, and (tetrahydrofuran-3-yl)methyl.

The term "hydroxy" or "hydroxyl" means an —OH group.

The term "hydroxyalkyl" means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "imino" means a —C(═NH)— group.

The term "mercapto" means a —SH group.

The term "nitro" means a —NO$_2$ group.

The term "oxo" means (═O).

The term "thioalkoxy" refers to an alkyl group, as defined herein, appended to the parent molecular moiety through a sulfur atom. Representative examples of thioalkoxy include, but are not limited to, methylthio, ethylthio, tert-butylthio, and hexylthio.

The term "thiocyloalkoxy" refers to an cycloalkyl group, as defined herein, appended to the parent molecular moiety through a sulfur atom. Representative examples of thiocylcloalkoxy include, but are not limited to, cyclopentylsulfane and cyclohexylsulfane.

The term "thiaryloxy" means an aryl group, as defined herein, appended to the parent molecular moiety through a sulfur atom. Representative examples of thioaryloxy include, but are not limited to, thiophenoxy and tolylsulfane.

The term "parenterally" refers to modes of administration, including intravenous, intramuscular, intraperitoneal, intrasternal, subcutaneous, intraarticular injection and infusion.

The term "Positive Allosteric Modulator (PAM)" means a compound that enhances activity of an endogenous ligand, such as but not limited to ACh, or an exogenously administered agonist.

The term "pharmaceutically acceptable salt" or "salt" refers to those salts which are, within the scope of sound medical judgment, suitable for use in contact with the tissues of humans and lower animals without undue toxicity, irritation, allergic response, and the like, and are commensurate with a reasonable benefit/risk ratio and effective for their intended use. Pharmaceutically acceptable salts are well-known in the art. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid. Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediammonium, ethanolammonium, diethanolammonium, piperidinium, and piperazinium.

The term "pharmaceutically acceptable ester" or "ester" refers to esters of compounds of the invention which hydrolyze in vivo and include those that break down readily in the human body to leave the parent compound or a salt thereof. Examples of pharmaceutically acceptable, non-toxic esters of the invention include, but are not limited to, $C_1$-to-$C_6$ alkyl esters and $C_5$-to-$C_7$ cycloalkyl esters. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" or "amide" refers to non-toxic amides of the invention derived from ammonia, primary $C_1$-to-$C_3$ alkyl amines, primary $C_4$-to-$C_6$ alkyl amines, secondary $C_1$-to-$C_2$ dialkyl amines and secondary $C_3$-to-$C_6$ dialkyl amines. In the case of secondary amines, the amine can also be in the form of a 5- or 6-membered heterocycle containing one nitrogen atom. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the invention in the form of a pharmaceutically acceptable prodrug.

The term "pharmaceutically acceptable prodrug" or "prodrug" represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "pharmaceutically acceptable carrier" or "carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The phrase "therapeutically effective amount" means a sufficient amount of the compound to treat disorders, at a reasonable benefit/risk ratio applicable to any medical treatment.

Although typically it may be recognized that an asterisk is used to indicate that the exact subunit composition of a receptor is uncertain, for example α3β4* indicates a receptor that contains the α3 and β4 proteins in combination with other subunits, the term α7 as used herein is intended to include receptors wherein the exact subunit composition is both certain and uncertain. For example, as used herein α7 includes homomeric $(α7)_5$ receptors and α7* receptors, which denote an NNR containing at least one α7 subunit.

Compounds of the Invention

An embodiment relates to compounds of formula (I):

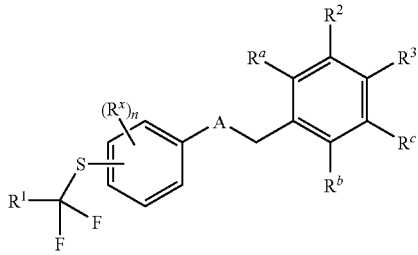

wherein,

A is —C(O)NH— or —NHC(O)—;

$R^a$, $R^b$, and $R^c$ are independently hydrogen, alkenyl, alkoxy, alkoxycarbonyl, alkyl, alkylcarbonyl, alkylsulfonyl, alkylthio, cyano, haloalkoxy, haloalkyl, or halogen;

$R^x$ at each occurrence is independently selected from the group consisting of acyloxy, alkoxy, alkyl, haloalkyl, halogen, and hydroxy;

n is 0, 1, 2, 3, or 4;

$R^1$ is hydrogen or halogen;

$R^2$ and $R^3$ are independently hydrogen, alkenyl, alkoxy, alkoxycarbonyl, alkyl, alkylcarbonyl, alkylsulfonyl, alkylthio, cyano, haloalkoxy, haloalkyl, halogen or $NR^5R^6$, provided that at least one of $R^2$ or $R^3$ is $NR^5R^6$;

$R^5$ and $R^6$ are independently hydrogen, alkenyl, alkoxyalkyl, alkoxycarbonyl, alkyl, alkylcarbonyl, alkylsulfonyl, arylalkyl, cycloalkyl, cycloalkylalkyl, haloalkyl, heteroarylalkyl, heterocycle, or heterocyclealkyl; or $R^5$, $R^6$ and the nitrogen atom to which they are attached form an optionally substituted monocyclic heteroaryl or an optionally substituted monocyclic heterocycle;

or pharmaceutically acceptable salts, esters, amides or prodrugs thereof.

Another embodiment is a compound of formula (I), wherein A is —C(O)NH—, or a pharmaceutically acceptable salt, ester, amide or prodrug thereof.

Another embodiment is a compound of formula (I), wherein A is —NHC(O)—, or a pharmaceutically acceptable salt, ester, amide or prodrug thereof.

Another embodiment is a compound of formula (I), wherein $R^a$, $R^b$ and $R^c$ are independently hydrogen or halogen, or a pharmaceutically acceptable salt, ester, amide or prodrug thereof.

Another embodiment is a compound of formula (I), wherein $R^x$ is acyloxy, alkoxy, halogen, or hydroxy, and n is 1, or a pharmaceutically acceptable salt, ester, amide or prodrug thereof. In another embodiment of the invention, halogen is fluorine or chlorine.

Another embodiment is a compound of formula (I), wherein $R^1$ is hydrogen, or a pharmaceutically acceptable salt, ester, amide or prodrug thereof.

Another embodiment is a compound of formula (I), wherein $R^1$ is fluorine, or a pharmaceutically acceptable salt, ester, amide or prodrug thereof. Another embodiment is a compound of formula (I), wherein one of $R^2$ or $R^3$ is hydrogen and the other is $NR^5R^6$, wherein $R^5$ and $R^6$ are independently selected from hydrogen, alkoxycarbonyl, alkyl, alkylcarbonyl, alkylsulfonyl, arylalkyl, cycloalkyl, cycloalkylalkyl, haloalkyl, heteroarylalkyl and heterocycle, or a pharmaceutically acceptable salt, ester, amide or prodrug thereof. In another embodiment of the invention, one of $R^5$ and $R^6$ is alkyl and the other is hydrogen or alkyl.

Another embodiment is a compound of formula (I), wherein one of $R^2$ or $R^3$ is hydrogen and the other is $NR^5R^6$, wherein $R^5$ and $R^6$ and the nitrogen atom to which they are attached form a monocyclic heteroaryl, or a pharmaceutically acceptable salt, ester, amide or prodrug thereof. In a further embodiment of the invention, monocyclic heteroaryls are imidazole, pyrazole, and pyrrole.

Another embodiment is a compound of formula (I), wherein one of $R^2$ or $R^3$ is hydrogen and the other is $NR^5R^6$, wherein $R^5$ and $R^6$ and the nitrogen atom to which they are attached form a monocyclic heterocycle, or a pharmaceutically acceptable salt, ester, amide or prodrug thereof. In an embodiment of the invention, monocyclic heterocycles are azetidine, diazepane, piperidine, and pyrrolidine.

Another embodiment is a compound of formula (I), wherein A is —C(O)NH—, $R^1$ is hydrogen or fluorine, and one of $R^2$ or $R^3$ is hydrogen and the other is $NR^5R^6$, wherein $R^5$ is alkyl and $R^6$ is hydrogen or alkyl, or a pharmaceutically acceptable salt, ester, amide or prodrug thereof.

Another embodiment is a compound of formula (I), wherein A is —C(O)NH—, $R^1$ is hydrogen or fluorine, and one of $R^2$ or $R^3$ is hydrogen and the other is $NR^5R^6$, wherein $R^5$ is hydrogen or alkyl and $R^6$ is alkylcarbonyl or alkylsulfonyl, or a pharmaceutically acceptable salt, ester, amide or prodrug thereof.

Another embodiment is a compound of formula (I), wherein A is —C(O)NH—, $R^1$ is hydrogen or fluorine, and one of $R^2$ or $R^3$ is hydrogen and the other is $NR^5R^6$, wherein $R^5$ and $R^6$ and the nitrogen atom to which they are attached form a monocyclic heterocycle, or a pharmaceutically acceptable salt, ester, amide or prodrug thereof.

Another embodiment is a compound of formula (I), wherein A is —C(O)NH—, $R^1$ is hydrogen or fluorine, and one of $R^2$ or $R^3$ is hydrogen and the other is $NR^5R^6$, wherein $R^5$ and $R^6$ and the nitrogen atom to which they are attached form a monocyclic heteroaryl, or a pharmaceutically acceptable salt, ester, amide or prodrug thereof.

Another embodiment is a compound of formula (I), wherein A is —NHC(O)—, $R^1$ is hydrogen or fluorine, and one of $R^2$ or $R^3$ is hydrogen and the other is $NR^5R^6$, wherein $R^5$ and $R^6$ are independently hydrogen, alkoxycarbonyl, alkyl, or haloalkyl, or a pharmaceutically acceptable salt, ester, amide or prodrug thereof.

Another embodiment is a compound of formula (I), wherein A is —NHC(O)—, $R^1$ is hydrogen or fluorine, and one of $R^2$ or $R^3$ is hydrogen and the other is $NR^5R^6$, wherein $R^5$ is hydrogen and $R^6$ cycloalkyl or heterocycle, or a pharmaceutically acceptable salt, ester, amide or prodrug thereof.

Another embodiment is a compound of formula (I), wherein A is —NHC(O)—, $R^1$ is hydrogen or fluorine, and one of $R^2$ or $R^3$ is hydrogen and the other is $NR^5R^6$, wherein $R^5$ is hydrogen and $R^6$ arylalkyl, cycloalkylalkyl, or heteroarylalkyl, or a pharmaceutically acceptable salt, ester, amide or prodrug thereof.

Another embodiment is a compound of formula (I), wherein the monocyclic heteroaryl is optionally substituted with 0, 1, 2, or 3 substituents selected from acyloxy, alkenyl, alkoxy, alkoxycarbonyl, alkyl, alkylcarbonyl, alkylsulfonyl, alkylthio, alkynyl, amido, cyano, cyanoalkyl, cycloalkyl, haloalkoxy, haloalkyl, halogen, nitro, and —$NR^7R^8$; wherein $R^7$ and $R^8$ are independently acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, haloalkyl, halocycloalkyl, halocycloalkylalkyl, heteroaryl, heterocycle, hydrogen, formyl, hydroxy, or hydroxyalkyl In a further embodiment, $R^7$ and $R^8$ are independently hydrogen, alkoxyalkyl, alkoxycarbonyl, alkyl, alkylcarbonyl, alkylsulfonyl, aryl, cycloalkyl, haloalkyl, heteroaryl, or heterocycle.

Another embodiment is a compound of formula (I), wherein the monocyclic heterocycle can be optionally substituted with 0, 1, 2, or 3 substituents selected from the group consisting of acyloxy, alkenyl, alkoxy, alkoxycarbonyl, alkyl, alkylcarbonyl, alkylsulfonyl, alkylthio, alkynyl, amido, cyano, cyanoalkyl, cycloalkyl, haloalkoxy, haloalkyl, halogen, nitro, oxo, and —$NR^{98}R^{99}$, wherein $R^{98}$ and $R^{99}$ are independently hydrogen, acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, haloalkyl, halocycloalkyl, halocycloalkylalkyl, heteroaryl, heterocycle, hydrogen, formyl, hydroxy, or hydroxyalkyl.

In a further embodiment, —$NR^{98}R^{99}$ are independently hydrogen, alkoxyalkyl, alkoxycarbonyl, alkyl, alkylcarbonyl, alkylsulfonyl, aryl, cycloalkyl, haloalkyl, heteroaryl, or heterocycle.

Exemplary compounds of various embodiments include, but are not limited to:

N-[3-(1H-pyrrol-1-yl)benzyl]-4-[(trifluoromethyl)thio]benzamide;
N-(3-piperidin-1-ylbenzyl)-4-[(trifluoromethyl)thio]benzamide;
N-(3-pyrrolidin-1-ylbenzyl)-4-[(trifluoromethyl)thio]benzamide;
N-[4-(4-methyl-1,4-diazepan-1-yl)benzyl]-4-[(trifluoromethyl)thio]benzamide;
N-[4-(acetylamino)benzyl]-4-[(trifluoromethyl)thio]benzamide;
N-[4-(diethylamino)benzyl]-4-[(trifluoromethyl)thio]benzamide;
N-[4-(2-methyl-1H-imidazol-1-yl)benzyl]-4-[(trifluoromethyl)thio]benzamide;
N-{3-[(methylsulfonyl)amino]benzyl}-4-[(trifluoromethyl)thio]benzamide;
N-[3-(methylamino)benzyl]-4-[(trifluoromethyl)thio]benzamide;
N-[4-(2-oxopyrrolidin-1-yl)benzyl]-4-[(trifluoromethyl)thio]benzamide;
N-{4-[(methylsulfonyl)amino]benzyl}-4-[(trifluoromethyl)thio]benzamide;
N-[3-(1H-pyrazol-1-yl)benzyl]-4-[(trifluoromethyl)thio]benzamide;
N-[4-(3,5-dimethyl-1H-pyrazol-1-yl)benzyl]-4-[(trifluoromethyl)thio]benzamide;
N-[3-(dimethylamino)benzyl]-4-[(trifluoromethyl)thio]benzamide;
N-{3-[acetyl(methyl)amino]benzyl}-4-[(trifluoromethyl)thio]benzamide;
N-[4-(1H-pyrrol-1-yl)benzyl]-4-[(trifluoromethyl)thio]benzamide;
N-[4-(dimethylamino)benzyl]-4-[(trifluoromethyl)thio]benzamide;
N-(4-pyrrolidin-1-ylbenzyl)-4-[(trifluoromethyl)thio]benzamide;
N-(4-aminobenzyl)-4-[(trifluoromethyl)thio]benzamide;
N-[4-(methylamino)benzyl]-4-[(trifluoromethyl)thio]benzamide;
4-[(difluoromethyl)thio]-N-[4-(dimethylamino)benzyl]benzamide;
4-[(difluoromethyl)thio]-N-[4-(methylamino)benzyl]benzamide;
N-{4-[(difluoromethyl)thio]phenyl}-2-(4-pyrrolidin-1-ylphenyl)acetamide;
N-{4-[(difluoromethyl)thio]phenyl}-2-(4-piperidin-1-ylphenyl)acetamide;
2-(4-azetidin-1-ylphenyl)-N-{4-[(difluoromethyl)thio]phenyl}acetamide;
2-[4-(3,3-difluoroazetidin-1-yl)phenyl]-N-{4-[(difluoromethyl)thio]phenyl}acetamide;
tert-butyl 4-[2-({4-[(difluoromethyl)thio]phenyl}amino)-2-oxoethyl]phenyl carbamate;
2-(4-aminophenyl)-N-{4-[(difluoromethyl)thio]phenyl}acetamide;
N-{4-[(difluoromethyl)thio]phenyl}-2-[4-(methylamino)phenyl]acetamide;
N-{4-[(difluoromethyl)thio]phenyl}-2-[4-(dimethylamino)phenyl]acetamide;
2-[4-(dimethylamino)phenyl]-N-{4-[(trifluoromethyl)thio]phenyl}acetamide;
N-{4-[(difluoromethyl)thio]phenyl}-2-[4-(isobutylamino)phenyl]acetamide;
2-{4-[(cyclohexylmethyl)amino]phenyl}-N-{4-[(difluoromethyl)thio]phenyl}acetamide;
N-{4-[(difluoromethyl)thio]phenyl}-2-{4-[(2-methoxybenzyl)amino]phenyl}acetamide;
2-{4-[(4-chlorobenzyl)amino]phenyl}-N-{4-[(difluoromethyl)thio]phenyl}acetamide;
2-{4-[(2-chlorobenzyl)amino]phenyl}-N-{4-[(difluoromethyl)thio]phenyl}acetamide;
N-{4-[(difluoromethyl)thio]phenyl}-2-{4-[(3-methoxybenzyl)amino]phenyl}acetamide;
N-{4-[(difluoromethyl)thio]phenyl}-2-{4-[(3-methylbutyl)amino]phenyl}acetamide;
N-{4-[(difluoromethyl)thio]phenyl}-2-{4-[(quinolin-4-ylmethyl)amino]phenyl}acetamide;
N-{4-[(difluoromethyl)thio]phenyl}-2-(4-{[(5-ethyl-2-furyl)methyl]amino}phenyl)acetamide;
N-{4-[(difluoromethyl)thio]phenyl}-2-[4-(tetrahydro-2H-pyran-4-ylamino)phenyl]acetamide;
N-{4-[(difluoromethyl)thio]phenyl}-2-{4-[(4-phenoxybenzyl)amino]phenyl}acetamide;
2-{4-[(cyclopropylmethyl)amino]phenyl}-N-{4-[(difluoromethyl)thio]phenyl}acetamide;
2-(4-{[(4-bromothien-2-yl)methyl]amino}phenyl)-N-{4-[(difluoromethyl)thio]phenyl}acetamide;
N-{4-[(difluoromethyl)thio]phenyl}-2-{4-[(quinolin-2-ylmethyl)amino]phenyl}acetamide;
2-(4-{[(1-acetyl-1H-indol-3-yl)methyl]amino}phenyl)-N-{4-[(difluoromethyl)thio]phenyl}acetamide;
2-[4-(cyclohexylamino)phenyl]-N-{4-[(difluoromethyl)thio]phenyl}acetamide;
2-[4-({[5-(2-chlorophenyl)-2-furyl]methyl}amino)phenyl]-N-{4-[(difluoromethyl)thio]phenyl}acetamide;
N-{4-[(difluoromethyl)thio]phenyl}-2-{4-[(4-methoxybenzyl)amino]phenyl}acetamide;
2-[4-(cyclopentylamino)phenyl]-N-{4-[(difluoromethyl)thio]phenyl}acetamide;
2-{4-[(3-chlorobenzyl)amino]phenyl}-N-{4-[(difluoromethyl)thio]phenyl}acetamide;
2-[4-(cyclobutylamino)phenyl]-N-{4-[(difluoromethyl)thio]phenyl}acetamide;
2-[4-(cycloheptylamino)phenyl]-N-{4-[(difluoromethyl)thio]phenyl}acetamide;
N-{4-[(difluoromethyl)thio]phenyl}-2-{4-[(2-methylbutyl)amino]phenyl}acetamide;
N-{4-[(difluoromethyl)thio]phenyl}-2-(4-{[(5-methylthien-2-yl)methyl]amino}phenyl)acetamide;
N-{4-[(difluoromethyl)thio]phenyl}-2-{4-[(2-naphthylmethyl)amino]phenyl}acetamide;

N-{4-[(difluoromethyl)thio]phenyl}-2-{4-[(3,3,5,5-tetramethylcyclohexyl)amino]phenyl}acetamide;
N-{4-[(difluoromethyl)thio]phenyl}-2-{4-[(thien-2-ylmethyl)amino]phenyl}acetamide;
N-{4-[(difluoromethyl)thio]phenyl}-2-[4-(neopentylamino)phenyl]acetamide;
N-{4-[(difluoromethyl)thio]phenyl}-2-(4-{[4-(trifluoromethyl)cyclohexyl]amino}phenyl)acetamide;
N-{4-[(difluoromethyl)thio]phenyl}-2-{4-[(2,2,2-trifluoroethyl)amino]phenyl}acetamide; and
N-{4-[(difluoromethyl)thio]phenyl}-2-{4-[(3-phenylcyclohexyl)amino]phenyl}acetamide.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds including geometric isomers of carbon-carbon double bonds and carbon-nitrogen double bonds are included in the present invention. Substituents around a carbon-carbon or a carbon-nitrogen double bond are designated as being of Z or E configuration and substituents around a cycloalkyl or heterocycle are designated as being of cis or trans configuration. All geometric isomeric forms and mixtures thereof of the compounds described herein are encompassed within the scope of the present invention.

Compounds of the invention can exist in radiolabeled or isotope labeled form containing one or more atoms having an atomic mass or mass number different from the atomic mass or mass number most abundantly found in nature. Isotopes of atoms such as hydrogen, carbon, phosphorous, sulfur, fluorine, chlorine, and iodine include, but are not limited to, $^2$H, $^3$H, $^{14}$C, $^{32}$P, $^{35}$S, $^{18}$F, $^{36}$Cl, and $^{125}$I. Compounds that contain other radioisotopes of these and/or other atoms are within the scope of this invention. In an embodiment of the invention, the isotope-labeled compounds contain deuterium ($^2$H), tritium ($^3$H) or $^{14}$C radioisotopes. Isotope and radiolabeled compounds of this invention can be prepared by the general methods well known to persons having ordinary skill in the art. Such isotope and radiolabeled compounds can be conveniently prepared by carrying out the procedures disclosed in the above Examples and Schemes by substituting a readily available isotope or radiolabeled reagent for a non-labeled reagent. The isotope and radiolabeled compounds of the invention may be used as standards to determine the effectiveness of α7 NNR ligands or modulators in the binding assays.

Amides, Esters and Prodrugs

Prodrugs are pharmacologically inactive derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

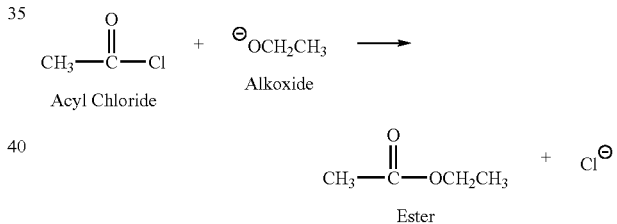

Amides can be prepared from substrates of formula (I) containing either an amino group or a carboxy group in similar fashion. Esters can also react with amines or ammonia to form amides.

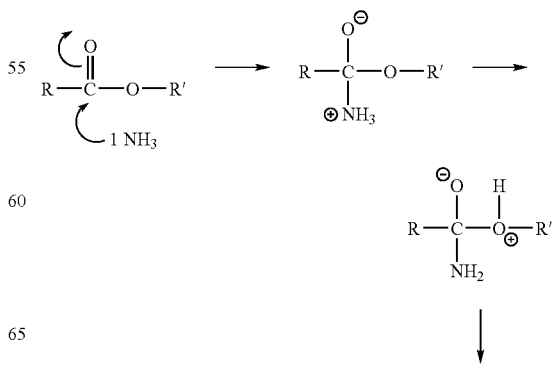

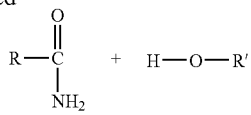

Another way to make amides from compounds of formula (I) is to heat carboxylic acids and amines together.

Scheme 3

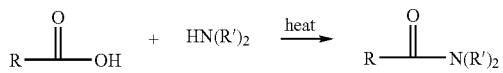

In Schemes 2 and 3, R and R' are independently substrates of formula (I), alkyl or hydrogen. Various embodiments of formula (I) that are substrates for prodrugs, amides and esters include, but not limited to, Examples 9, 19, 20, 22, 28, 29, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, and 62. Examples 5, 15, 27, and 46 are representative prodrugs of the invention.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or in a certain part of the intestinal tract in a delayed manner. Examples of materials useful for delaying release of the active agent can include polymeric substances and waxes.

In an embodiment of the invention, compositions for rectal or vaginal administration are suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds and compositions of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. In one embodiment of the invention, lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq., which is incorporated herein by reference.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

Yet another embodiment relates to radiolabelled or isotopically labelled pharmaceutical compositions comprising radiolabelled or isotopically labelled forms of compounds of formula (I).

Methods of the Invention

Compounds and compositions of the invention are useful for modulating the effects of NNRs, particularly by allosteric modulation. Such compounds can be useful for the treatment and prevention of a number of NNR-mediated diseases or conditions.

$\alpha 7$ NNRs have been shown to play a significant role in enhancing cognitive function, including aspects of learning, memory and attention (Levin, E. D., *J. Neurobiol.*, 2002, 53: 633-640). As such, $\alpha 7$ ligands are suitable for the treatment of cognitive disorders including, for example, attention deficit disorder, ADHD, AD, MCI, senile dementia, AIDS dementia, Pick's disease, dementia associated with Lewy bodies, and dementia associated with Down's syndrome, as well as cognitive deficits associated with schizophrenia.

In addition, $\alpha 7$ NNRs have been shown to be involved in the neuroprotective effects of nicotine both in vitro (Jonnala, R. B., et al., *J. Neurosci. Res.*, 2001, 66: 565-572) and in vivo (Shimohama, S., *Brain Res.*, 1998, 779: 359-363). More particularly, neurodegeneration underlies several progressive CNS disorders, including, but not limited to, AD, Parkinson's disease, amyotrophic lateral sclerosis, Huntington's disease, dementia with Lewy bodies, as well as diminished CNS function resulting from traumatic brain injury. For example, the impaired function of $\alpha 7$ NNRs by $\beta$-amyloid peptides linked to AD has been implicated as a key factor in development of the cognitive deficits associated with the disease (Liu, Q.-S., et al., *PNAS*, 2001, 98: 4734-4739). The activation of $\alpha 7$ NNRs has been shown to block this neurotoxicity (Kihara, T., *J. Biol. Chem.*, 2001, 276: 13541-13546). As such, selective ligands that enhance $\alpha 7$ activity can counter the deficits of Alzheimer's and other neurodegenerative diseases.

Schizophrenia is a complex disease that is characterized by abnormalities in perception, cognition, and emotions. Significant evidence implicates the involvement of $\alpha 7$ NNRs in this disease, including a measured deficit of these receptors in post-mortem patients (Leonard, S., *Eur. J. Pharmacol.*, 2000, 393: 237-242). Deficits in sensory processing (gating) are one of the hallmarks of schizophrenia. These deficits can be normalized by nicotinic ligands that operate at the $\alpha 7$ NNR (Adler, L. E., *Schizophrenia Bull.*, 1998, 24: 189-202; Stevens, K. E., *Psychopharmacology*, 1998, 136: 320-327). Thus, $\alpha 7$ NNR ligands demonstrate potential in the treatment of schizophrenia.

A population of $\alpha 7$ NNRs in the spinal cord modulate serotonergic transmission that have been associated with the pain-relieving effects of nicotinic compounds (Cordero-Erausquin, M., et al., *Proc. Nat. Acad. Sci.*, 2001, 98: 2803-2807). The $\alpha 7$ NNR ligands demonstrate therapeutic potential for the treatment of pain states, including acute pain, post-surgical pain, as well as chronic pain states including inflammatory pain and neuropathic pain. Moreover, α7 NNRs are expressed on the surface of primary macrophages that are involved in the inflammation response, and that activation of the α7 NNR inhibits release of tumor necrosis factor (TNF) and other cytokines that trigger the inflammation response (Wang, H., *Nature,* 2003, 421: 384-388). TNF-α plays a pathological role in diverse inflammatory diseases including arthritis and psoriasis and endometriosis. Therefore, selective α7 NNR ligands and modulators demonstrate potential for treating conditions involving inflammation and pain.

Compounds of the invention are useful for treating and preventing a condition or disorder affecting cognition, neurodegeneration, and schizophrenia. Cognitive impairment associated with schizophrenia often limits the ability of patients to function normally; a symptom not adequately treated by commonly available treatments, for example, treatment with an atypical antipsychotic (Rowley, M., *J. Med. Chem.,* 2001, 44: 477-501). Such cognitive deficit has been linked to dysfunction of the nicotinic cholinergic system, in particular with decreased activity at α7 NNR receptors (Friedman, J. I., *Biol. Psychiatry,* 2002, 51: 349-357). Thus, activators of α7 NNR receptors can provide useful treatment for enhancing cognitive function in schizophrenic patients who are being treated with atypical antipsychotics. Accordingly, the combination of an α7 NNR modulator and an atypical antipsychotic would offer improved therapeutic utility.

Examples of suitable atypical antipsychotics include, but are not limited to, clozapine, risperidone, olanzapine, quietapine, ziprasidone, zotepine, iloperidone, and the like. Accordingly, it is contemplated that compounds of formula (I) also can be administered in combination with an atypical antipsychotic.

One of the measurable abnormalities in schizophrenic patients is the P50 auditory gating deficit, an indication of impaired information processing and diminished ability to "filter" unimportant or repetitive sensory information. On the basis of clinical observations that these deficits are normalized by nicotine, it has been suggested that the high prevalence of smoking among patients with schizophrenia (>80%) may be a form of self-medication. Pharmacological studies have shown that nicotine's mechanism of action is via α7 NNRs. Restoration of P50 gating deficits in humans by α7 selective ligands, agonists and PAMs could lead to discontinuation of continuous smoking. Therefore, NNR ligands that are selective for the α7 subtype and can be used in therapy for smoking cessation, with an improved side effect profile compared to nicotine.

An embodiment is a method of using compounds of formula (I) or pharmaceutically acceptable salts, esters, amides or prodrugs thereof for treating or preventing conditions and disorders related to NNR modulation or regulation in mammals. In another embodiment of the invention, the method is useful for treating or preventing conditions and disorders modulated by α7 NNRs modulators.

The conditions and disorders related to NNR modulation or regulation include, but are not limited to, attention deficit disorder, ADHD, AD, MCI, schizophrenia, senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammation, inflammatory pain, neuropathic pain, smoking cessation, depression, and various other conditions.

Another embodiment is a method of administration of a therapeutically effective amount of a compound of formula (I) or a pharmaceutically acceptable salt, ester, amide or prodrug thereof to a mammal in need thereof for treating or preventing a condition or disorder selected from attention deficit disorder, ADHD, AD, MCI, senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammation, inflammatory pain, neuropathic pain, and depression.

Combination of exogenously applied nicotinic ligands such as α7 and α4β2 NNR ligands, along with a PAM would be expected to boost beneficial effects. Accordingly, another embodiment relates to a method of using compounds of formula (I) or pharmaceutically acceptable salts, esters, amides or prodrugs thereof for treating or preventing conditions and disorders related to NNR modulation or regulation in mammals in combination with at least one of α7 NNR and α4β2 NNR ligands.

An embodiment is a method of treating a disorder or condition modulated or regulated by α7 NNRs comprising administering the compound of formula (I) or a pharmaceutically acceptable salt, ester, amide or prodrug thereof as a stand-alone product to be combined with an α7 or α4β2 NNR ligand or as a component of a fixed dose combination product with an α7 or α4β2 NNR ligand.

Another embodiment is a method of administering the compositions containing compounds of formula (I) or pharmaceutically acceptable salts, esters, amides or prodrugs thereof in combination with a nicotinic ligand either co-dosed or in a formulation in combination with a nicotinic agonist.

Examples of nicotinic ligands include, but are not limited to, 5-[(2R)-azetidin-2-ylmethoxy]-2-chloro pyridine; (3R)-1-pyridin-3-ylpyrrolidin-3-amine; 2-methyl-3-(2-(S)-pyrrolidinyl methoxy)pyridine; 3-(5,6-dichloro-pyridin-3-yl)-(1S,5S)-3,6-diazabicyclo[3.2.0]heptane; (R,R)-1-(pyridin-3-yl) octahydro-pyrrolo[3,4-b]pyrrole; 6,10-methano-6H-pyrazino[2,3-h][3]benzazepine; 7,8,9,10-tetrahydro-(2S,4E)-N-methyl-5-(5-isopropoxy-3-pyridyl)-4-penten-2-amine; (2S,4E)-N-methyl-5-(5-methoxy-3-pyridyl)-4-penten-2-amine; (2S,4E)-N-methyl-5-(5-ethoxy-3-pyridyl)-4-penten-2-amine; (2S,4E)-N-methyl-3-pyrimidine-4-penten-2-amine; (5aS,8S,10aR)-5a,6,9,10-tetrahydro-7H,11H-8,10a-methanopyrido[2',1':5,6]pyran[2,3-d]azepine; 3-[1-(2,4-dimethoxy-phenyl)-meth-(E)-ylidene]-3,4,5,6-tetrahydro-[2,3]bipyridinyl; 3-[1-(2-methoxy-4-hydroxyphenyl)-meth-(E)-ylidene]-3,4,5,6-tetrahydro-[2,3']bipyridinyl; and 4-bromophenyl 1,4-diazabicyclo[3.2.2]nonane-4-carboxylate.

An embodiment relates to a method of using compositions or compounds of formula (I), or pharmaceutically acceptable salts, esters, amides or prodrugs thereof, in combination with a cholinesterase inhibitor or another drug that increases endogenous acetylcholine release such as histamine H3 antagonists, 5HT-6 antagonists, dopamine D1 agonists, muscarinic receptor antagonists and potassium channel blockers, leading to potentiation of effects at the α7 nicotinic receptor subtype.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds can be employed in pure form or, where such forms exist, in pharmaceutically acceptable salt, ester, amide or prodrug form. Alternatively, the compound can be administered as a pharmaceutical composition containing the compound of the invention or pharmaceutically acceptable salt, ester, amide or prodrug in combination with one or more pharmaceutically acceptable carriers.

It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal ranges from about 0.001 mg/kg body weight to about 1 g/kg body weight. Doses can be in the range of from about 0.001 mg/kg body weight to about 100 mg/kg body weight. If desired, the effective daily dose can be divided into multiple doses for purposes of administration. Consequently, single dose compositions may contain such amounts or submultiples thereof to make up the daily dose. When used in combination, co-administered or as a fixed dose combination, the doses may be adjusted to achieve maximal benefit.

Another embodiment relates to a method of assessing or diagnosing conditions or disorders related to α7 NNR activity comprising allowing isotope-labeled forms of compounds of formula (I) to interact with cells expressing endogenous α7 NNRs or cells expressing recombinant α7 NNRs, and measuring the effects of such isotope-labeled forms of compounds on such cells. The radiolabeled compounds may be used as standards to determine the effectiveness of α7 NNR ligands or modulators in the binding assays described herein.

Various embodiments also describe the use of NNR ligands, and particularly PAM compounds, to identify other useful target compounds for treating or preventing, or both, diseases or conditions associated with NNR function, in cell-based assays, for example in high-throughput format, using cells or tissues that express native α7 NNRs for the purpose of identifying novel α7 NNR agonists or PAMs of α7 NNRs, by known protocols or as described in Determination of Biological Activity section.

Another embodiment is a method of identifying an α7 NNR agonist comprising allowing a compound of formula (I) to interact with cells or cell lines endogenously expressing α7 NNRs or cells expressing recombinant α7 NNRs in a fluorescent medium and measuring changes in such fluorescence by known protocols or as described in Determination of Biological Activity section.

Preparation of Compounds of Formula (I)

The methods described below can entail use of various enantiomers. The compounds of this invention can be prepared according to the synthetic methods described in this section, Methods of the Invention and Examples sections. Certain groups described in the Scheme are meant to illustrate certain substituents contained within the invention and are not intended to limit the scope of the invention. Representative procedures are shown in, but are not limited to, Schemes 4-6.

As outlined in Scheme 4, compounds of formula (3) which are representative of compounds of formula (I) wherein $R^1$, $R^2$, $R^3$, $R^x$, n, $R^a$, $R^b$ and $R^c$ are as defined in formula (I), can be prepared accordingly. Compounds of formula (1) when treated with compounds of formula (2) in a solvent such as N,N-dimethylformamide or N,N-dimethylacetamide in the presence of a base such as N,N-diisopropylethylamine or triethylamine and a coupling reagent such as O-(7-azabenzotriazol-1-yl)-N,N,N',N'-tetramethyluronium hexafluorophosphate at or near room temperature for a period of 6 to 24 hours furnishes compounds of formula (3) which are representative of compounds of formula (I).

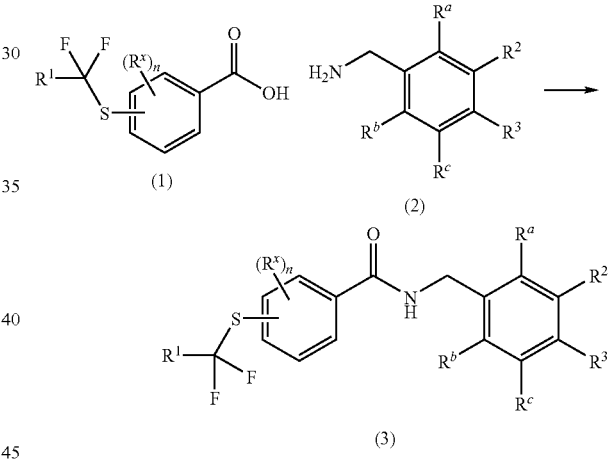

Scheme 4

Alternative conditions and reagents to form compounds of formula (3) include combining an equimolar mixture of the compounds of formula (1) and compounds of formula (2) with a coupling reagent such as but not limited to bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-benzotriazol-1-yl-N,N,N', N'-tetramethyluronium tetrafluoroborate (TBTU) optionally along with a coupling auxiliary such as but not limited to 1-hydroxy-7-azabenzotriazole (HOAT) or 1-hydroxybenzotriazole hydrate (HOBT) in the presence or absence of a base such as but not limited to N-methyl morpholine, diisopropylethylamine, and triethylamine in solvents such as, but not limited to, tetrahydrofuran, N,N-dimethylacetamide, N,N-dimethylformamide, pyridine and chloroform. Typical reactions can be carried out between 0-65° C. or may be carried out in a microwave reactor to facilitate the coupling.

Alternatively, the carboxylic acid of formula (1) may initially be converted to an acid chloride, typically by suspending the carboxylic acid in a solvent such as dichloromethane and then adding oxalyl chloride and a catalytic amount of N,N-dimethylformamide. The solvent may be removed by evaporation, and the acid chloride redissolved in pyridine. Addition of a compound of formula (2) in the presence of Hunig's base will furnish compounds of formula (3). The reaction may be conducted at ambient or elevated temperatures over a period ranging from several hours to several days.

As outlined in Scheme 5, compounds of formula (6) which are representative of compounds of formula (I) wherein $R^1$, $R^2$, $R^3$, $R^x$, n, $R^a$, $R^b$ and $R^c$ are as defined in formula (I), can be prepared accordingly.

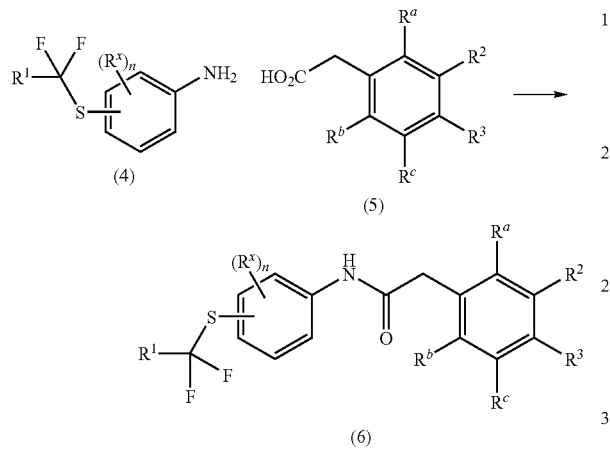

Compounds of formula (5) when treated with compounds of formula (4) in a solvent such as N,N-dimethylformamide or N,N-dimethylacetamide in the presence of a base such as N,N-diisopropylethylamine or triethylamine and a coupling reagent such as O-(7-azabenzotriazol-1-yl)-N,N,N',N'-tetramethyluronium hexafluorophosphate at or near room temperature for a period of 6 to 24 hours furnishes compounds of formula (6) which are representative of compounds of formula (I).

Alternative conditions and reagents to form compounds of formula (6) include combining an equimolar mixture of the compounds of formula (4) and compounds of formula (5) with a coupling reagent such as but not limited to bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-benzotriazol-1-yl-N,N,N',N'-tetramethyluronium tetrafluoroborate (TBTU) optionally along with a coupling auxiliary such as but not limited to 1-hydroxy-7-azabenzotriazole (HOAT) or 1-hydroxybenzotriazole hydrate (HOBT) in the presence or absence of a base such as but not limited to N-methyl morpholine, diisopropylethylamine, and triethylamine in solvents such as, but not limited to, tetrahydrofuran, N,N-dimethylacetamide, N,N-dimethylformamide, pyridine and chloroform. Typical reactions can be carried out between 0-65° C. or may be carried out in a microwave reactor to facilitate the coupling.

Alternatively, the carboxylic acid of formula (5) may initially be converted to an acid chloride, typically by suspending the carboxylic acid in a solvent such as dichloromethane and then adding oxalyl chloride and a catalytic amount of N,N-dimethylformamide. The solvent may be removed by evaporation, and the acid chloride redissolved in pyridine. Addition of a compound of formula (5) in the presence of Hunig's base will furnish compounds of formula (6). The reaction may be conducted at ambient or elevated temperatures over a period ranging from several hours to several days.

As outlined in Scheme 6, compounds of formula (9) which are representative of compounds of formula (I), wherein A, $R^1$, $R^2$, $R^3$, $R^x$, n, $R^a$, $R^b$, and $R^c$ are as defined in formula (I), can be prepared accordingly.

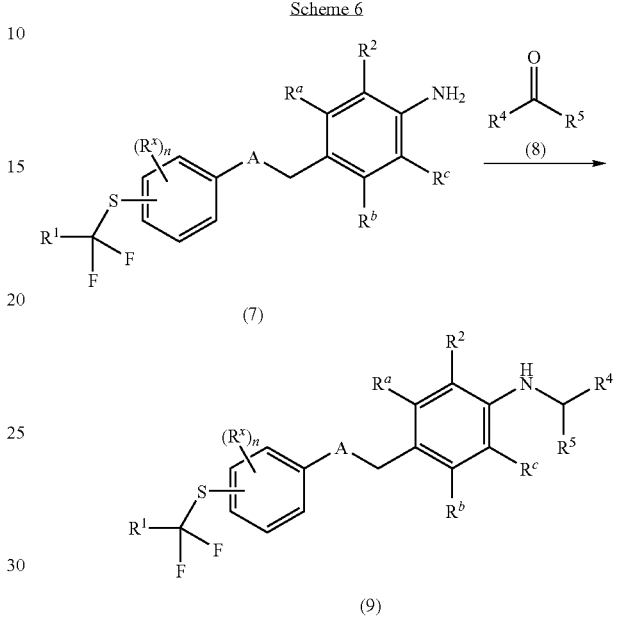

Compounds of formula (7) when treated with an aldehyde or ketone of formula (8), wherein $R^4$ and $R^5$ are independently hydrogen, alkyl, aryl, cycloalkyl, haloalkyl, heteroaryl or heterocycle or $R^4$ and $R^5$ and the carbon atom to which they are attached form a cycloalkyl or heterocycle, in a solvent mixture such as dichloromethane and methanol (1:1) in the presence of a reducing agent such as cyanoborohydride supported on a macroporous resin at a temperature of 20 to 60° C. in the presence of acetic acid from 2 to 24 hours supplies compounds of formula (9) which are representative of compounds of formula (I).

Alternative conditions and reagents to form compounds of formula (9) include combining mixtures of compounds of formula (7) and compounds of formula (8) in the presence of a reducing agent such as sodium cyanoborohydride, sodium borohydride, and sodium triacetoxyborohydride. Hydrogen, optionally at an increased pressure, in the presence of an appropriate catalyst such as palladium on carbon or platinum on carbon can also be the reductant. Sources of hydrogen include gaseous hydrogen, formic acid, cyclodienes such as cyclohexyldiene, or a salt of formic acid such as ammonium formate. When borohydride is used as the reducing agent, it can be advantageous to conduct the reaction in the presence of an acid such as, but not limited to, acetic acid or hydrochloric acid. Water scavenging reagents such as 4 A molecular sieves can enhance the reaction rate and completeness of the reaction. The reaction may be heated as described above to facilitate the reaction. Microwave heating also facilitates the reaction. Suitable solvents, for example, include esters (e.g., ethyl acetate, isopropyl acetate, and the like), ethers (e.g., tetrahydrofuran, diethylether, 1,4-dioxane, and the like), halogenated hydrocarbons (e.g., dichloromethane, trichloromethane, and the like), dipolar aprotic solvents (e.g., N,N- dimethylformamide, dimethyl sulfoxide and the like), and alcohols (e.g. methanol and the like), or a mixture of solvents thereof.

In addition, nitrogen protecting groups can be used for protecting amine groups during the synthesis of compounds of formula (I). Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation and acetyl and trifluoroacetyl protecting groups may be removed by variety of conditions including the use of sodium, potassium or lithium hydroxide in aqueous organic or alcoholic solvents.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss et al., pub. Longman Scientific & Technical, Essex CM20 2JE, England.

Some compounds of the invention have at least one basic site whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic acid, atrolactic acid, methanesulfonic acid, ethanesulfonic acid, toluenesulfonic acid, naphthalenesulfonic acid, carbonic acid, fumaric acid, gluconic acid, acetic acid, propionic acid, salicylic acid, hydrochloric acid, hydrobromic acid, phosphoric acid, sulfuric acid, citric acid, or hydroxybutyric acid, camphorsulfonic acid, malic acid, phenylacetic acid, aspartic acid, glutamic acid, and the like.

The invention contemplates pharmaceutically active compounds either chemically synthesized or formed by in vivo biotransformation to compounds of formula (I). The compounds, compositions, and methods of the invention will be better understood by reference to the following examples and reference examples, which are intended as an illustration of and not a limitation upon the scope of the invention.

EXAMPLES

Abbreviations

ACh for acetylcholine, DMSO for dimethyl sulfoxide, ERK for extracellular signal-regulated kinase, HPLC for high-pressure liquid chromatography, HEPES for 4-(2-hydroxyethyl)-1-piperazineethanesulfonic acid, PAM for positive allosteric modulator, PBS for phosphate buffered saline, SDS for sodium dodecyl sulfate, and Tween for polyoxoethylenesorbitan monolaurate.

General Procedure for Amide Formation (Method A):

In a 96 deep well plate, 4-(trifluoromethylthio)benzoic acid (23 mg, 0.10 mmol) was added dissolved in N,N-dimethylacetamide (0.4 mL), followed by O-(7-azabenzotriazol-1-yl)-N,N,N',N'-tetramethyluronium hexafluorophosphate (HATU) (48 mg, 0.12 mmol, 1.2 equivalents) dissolved in N,N-dimethylacetamide (0.3 mL), triethylamine (26 mg, 0.25 mmol, 2.4 equivalents) dissolved in N,N-dimethylacetamide (0.3 mL), and finally the amine (0.7 mL of a 0.2 M solution in N,N-dimethylacetamide, 1.4 equivalents). This was shaken at room temperature overnight. The reaction solution was concentrated to dryness in vacuo, dissolved in 1:1 dimethyl sulfoxide/methanol and purified by reverse phase HPLC on a Phenomenex® Luna® Combi-HTS C8(2) 5 μm 100 Å (2.1 mm×30 mm) using a gradient of 10-100% acetonitrile (A) and 0.1% trifluoroacetic acid (B) in water at a flow rate of 2.0 mL/minute (0-0.1 minutes 10% A, 0.1-2.6 minutes 10-100% A, 2.6-2.9 minutes 100% A, 2.9-3.0 minutes 100-10% A.) to give the product.

General Procedure for Amide Formation (Method B):

A suspension of an amine (0.5 mmol) and a benzoic acid (0.5 mmol) in anhydrous N,N-dimethylformamide (2 mL) was treated with N,N-diisopropylethylamine (iPr$_2$NEt; 245 μL, 1.5 mmol, 3.0 equivalents; Acros) and O-(7-azabenzotriazol-1-yl)-N,N,N',N'-tetramethyluronium hexafluorophosphate (HATU; 285 mg, 0.75 mmol, 1.5 equivalents; Aldrich). The mixture was stirred overnight at room temperature, and diluted with dichloromethane (20 mL). The solution was washed with dilute aqueous ammonium chloride (2×7 mL), dilute aqueous sodium bicarbonate (2×7 mL), and brine (2×7 mL). The organic layer was dried over sodium sulfate, filtered, and concentrated in vacuo. The resulting material was purified by either flash chromatography [Analogix pre-packed silica gel cartridges, 5-50% gradient of ethyl acetate/hexanes], or by preparative HPLC [Waters® Xterra® RP$_{18}$ 30×100 mm column, flow rate 40 mL/minute, 5-95% gradient of acetonitrile in buffer (0.1 M aqueous ammonium bicarbonate, adjusted to pH 10 with sodium hydroxide)] to afford the desired amide product as its free base. Alternatively, the compound was purified on a Waters® Symmetry® C$_8$ 30×100 mm column (flow rate 40 mL/minute, 5-95% gradient of acetonitrile in 0.1% aqueous trifluoroacetic acid) to afford the amide product after evaporation of solvent.

General Procedure for Amide Formation (Method C):

A solution of a phenylacetic acid (0.5 mmol, 1 equivalent) and O-(7-azabenzotriazol-1-yl)-N,N,N',N'-tetramethyluronium hexafluorophosphate (HATU; 285 mg, 0.75 mmol, 1.5 equivalent) in anhydrous N,N-dimethylformamide (2 mL) was treated with N,N-diisopropylethylamine (iPr$_2$NEt; 245 μL, 1.5 mmol, 3.0 equivalent) and 4-(difluoromethylthio)aniline (0.5 mmol, 1 equivalent). The mixture was stirred overnight at room temperature, and diluted with ethyl acetate (20 mL). The solution was washed with dilute aqueous ammonium chloride (2×7 mL), dilute aqueous sodium bicarbonate (2×7 mL), and brine (2×7 mL). The organic layer was dried over sodium sulfate, filtered, and concentrated in vacuo. The resulting material was purified by either flash chromatography [Analogix pre-packed silica gel cartridges, 5-50% gradient of ethyl acetate/hexanes], or by preparative HPLC [Waters® Xterra® RP$_{18}$ 30×100 mm column, flow rate 40 mL/minute, 5-95% gradient of acetonitrile in buffer (0.1 M aqueous ammonium bicarbonate, adjusted to pH 10 with sodium hydroxide)] to afford the desired amide product as its free base.

Alternatively, the compound was purified on a Waters® Symmetry® C$_8$ 30×100 mm column (flow rate 40 mL/minute, 5-95% gradient of acetonitrile in 0.1% aqueous trifluoroacetic acid) to afford the amide product after evaporation of solvent.

General Procedure for Reductive Amination (Method D):

To a solution of 2-(4-aminophenyl)-N-{4-[(difluoromethyl)thio]phenyl}acetamide trifluoroacetate (Example 28) (50 mg, 0.12 mmol in 1.0 mL methanol/dichloromethane; 1:1) was added a solution of the aldehyde or ketone (0.14 mmol in 1.0 mL methanol/dichloromethane; 1:1). To this mixture, acetic acid (34 µL, 0.59 mmol) and macroporous resin supported cyanoborohydride (2.24 mmol/g, 158 mg, 0.36 mmol) were added and the mixture was shaken at 55° C. overnight. After cooling, the resin was removed by filtration, washed with methanol (2×2 mL), and the combined filtrate was concentrated under reduced pressure. The crude product was purified by reverse-phase preparative HPLC [Phenomenex® Luna® C8(2) 5 µm 100 Å AXIA™ column (30 mm×75 mm), (flow rate 50 mL/min, 10-100% gradient of acetonitrile in 0.1% aqueous trifluoroacetic acid)] to furnish the product after evaporation of the solvents.

Example 1

N-[3-(1H-pyrrol-1-yl)benzyl]-4-[(trifluoromethyl)thio]benzamide

The product was prepared from (3-(1H-pyrrol-1-yl)phenyl)methanamine according to Method A: $^1$H NMR (500 MHz, DMSO-d$_6$) δ ppm 4.54-4.58 (m, 2H), 6.28 (t, J=2.1 Hz, 2H), 7.22 (d, J=6.4 Hz, 1H), 7.32 (t, J=2.1 Hz, 2H), 7.38-7.47 (m, 2H), 7.51 (s, 1H), 7.81-7.87 (m, J=8.2 Hz, 2H), 7.96-8.03 (m, J=8.2 Hz, 2H), 9.32 (t, J=6.0 Hz, 1H); MS (ESI+) m/z 377.0 (M+H)$^+$.

Example 2

N-(3-piperidin-1-ylbenzyl)-4-[(trifluoromethyl)thio]benzamide

The product was prepared from (3-(piperidin-1-yl)phenyl)methanamine according to Method A: $^1$H NMR (500 MHz, DMSO-d$_6$) δ ppm 1.63-1.71 (m, 2H), 1.85-1.93 (m, 4H), 3.46-3.55 (m, 4H), 4.56 (s, 2H), 7.44 (t, J=3.7 Hz, 1H), 7.55 (d, J=4.3 Hz, 2H), 7.59 (s, 1H), 7.83-7.88 (m, J=8.2 Hz, 2H), 7.99-8.03 (m, J=8.2 Hz, 2H), 9.36 (t, J=5.8 Hz, 1H); MS (ESI+) m/z 395.1 (M+H)$^+$.

Example 3

N-(3-pyrrolidin-1-ylbenzyl)-4-[(trifluoromethyl)thio]benzamide

The product was prepared from (3-(pyrrolidin-1-yl)phenyl)methanamine according to Method A: $^1$H NMR (500 MHz, DMSO-d$_6$) δ ppm 1.90-1.99 (m, 4H), 3.18-3.26 (m, 4H), 4.43 (s, 2H), 6.51 (dd, J=7.9, 1.8 Hz, 1H), 6.60 (s, 1H), 6.63 (d, J=7.6 Hz, 1H), 7.15 (t, J=7.8 Hz, 1H), 7.82-7.86 (m, J=8.2 Hz, 2H), 7.93-8.04 (m, J=8.5 Hz, 2H); MS (ESI+) m/z 381.0 (M+H)$^+$.

Example 4

N-[4-(4-methyl-1,4-diazepan-1-yl)benzyl]-4-[(trifluoromethyl)thio]benzamide

The product was prepared from (4-(4-methyl-1,4-diazepan-1-yl)phenyl)methanamine according to Method A: $^1$H NMR (500 MHz, DMSO-d$_6$) δ ppm 2.03-2.23 (m, 2H), 2.84 (s, 3H), 3.12 (ddd, J=12.5, 11.2, 1.2 Hz, 1H), 3.18 (ddd, J=12.4, 10.7, 1.1 Hz, 1H), 3.35-3.48 (m, 2H), 3.52 (dd, J=13.0, 3.8 Hz, 1H), 3.60 (dd, J=15.6, 9.2 Hz, 1H), 3.72-3.79 (m, 2H), 4.37 (s, 2H), 6.70-6.76 (m, J=8.8 Hz, 2H), 7.16-7.22 (m, J=8.8 Hz, 2H), 7.79-7.85 (m, J=8.5 Hz, 2H), 7.93-7.98 (m, J=8.2 Hz, 2H); MS (ESI+) m/z 424.0 (M+H)$^+$.

Example 5

N-[4-(acetylamino)benzyl]-4-[(trifluoromethyl)thio]benzamide

The product was prepared from N-(4-(aminomethyl)phenyl)acetamide according to Method A: $^1$H NMR (500 MHz, DMSO-d$_6$) δ ppm 2.03 (s, 3H), 4.44 (d, J=5.2 Hz, 2H), 7.21-7.29 (m, J=8.8 Hz, 2H), 7.47-7.53 (m, J=8.5 Hz, 2H), 7.80-7.85 (m, J=8.2 Hz, 2H), 7.92-8.01 (m, J=8.5 Hz, 2H), 9.23 (t, J=6.0 Hz, 1H); MS (ESI+) m/z 369.0 (M+H)$^+$.

Example 6

N-[4-(diethylamino)benzyl]-4-[(trifluoromethyl)thio]benzamide

The product was prepared from 4-(aminomethyl)-N,N-diethylaniline according to Method A: $^1$H NMR (500 MHz, DMSO-d$_6$) δ ppm 1.01 (t, J=7.2 Hz, 6H), 3.58 (q, J=7.2 Hz, 4H), 4.56 (s, 2H), 7.50-7.57 (m, 4H), 7.83-7.88 (m, J=8.2 Hz, 2H), 7.97-8.03 (m, J=8.5 Hz, 2H), 9.36 (t, J=6.0 Hz, 1H); MS (ESI+) m/z 383.1 (M+H)$^+$.

Example 7

N-[4-(2-methyl-1H-imidazol-1-yl)benzyl]-4-[(trifluoromethyl)thio]benzamide

The product was prepared from (4-(2-methyl-1H-imidazol-1-yl)phenyl)methanamine according to Method A: $^1$H NMR (500 MHz, DMSO-d$_6$) δ ppm 2.52 (s, 3H), 4.60 (s, 2H), 7.56-7.62 (m, 4H), 7.71 (d, J=2.1 Hz, 1H), 7.80 (d, J=2.1 Hz, 1H), 7.84-7.89 (m, J=8.2 Hz, 2H), 7.98-8.05 (m, J=8.5 Hz, 2H), 9.43 (t, J=6.0 Hz, 1H); MS (ESI+) m/z 392.1 (M+H)$^+$.

Example 8

N-{3-[(methylsulfonyl)amino]benzyl}-4-[(trifluoromethyl)thio]benzamide

The product was prepared from N-(3-(aminomethyl)phenyl)methanesulfonamide according to Method A: $^1$H NMR (500 MHz, DMSO-d$_6$) δ ppm 2.97 (s, 3H), 4.48 (s, 2H), 7.10 (t, J=8.5 Hz, 2H), 7.18 (s, 1H), 7.32 (t, J=7.8 Hz, 1H), 7.81-7.87 (m, J=8.2 Hz, 2H), 7.96-8.01 (m, J=8.5 Hz, 2H), 9.28 (t, J=6.3 Hz, 1H), 9.73 (s, 1H); MS (ESI+) m/z 405.0 (M+H)$^+$.

Example 9

N-[3-(methylamino)benzyl]-4-[(trifluoromethyl)thio]benzamide

The product was prepared from 3-(aminomethyl)-N-methylaniline according to Method A: $^1$H NMR (500 MHz, DMSO-d$_6$) δ ppm 2.87 (s, 3H), 4.51 (s, 2H), 7.13 (d, J=7.9 Hz, 1H), 7.19 (s, 1H), 7.21 (d, J=7.9 Hz, 1H), 7.41 (t, J=7.8

Hz, 1H), 7.85 (m, J=8.2 Hz, 2H), 8.00 (m, J=8.5 Hz, 2H), 9.32 (t, J=6.3 Hz, 1H); MS (ESI+) m/z 341.0 (M+H)$^+$.

Example 10

N-[4-(2-oxopyrrolidin-1-yl)benzyl]-4-[(trifluoromethyl)thio]benzamide

The product was prepared from 1-(4-(aminomethyl)phenyl)pyrrolidin-2-one according to Method A: $^1$H NMR (500 MHz, DMSO-d$_6$) δ ppm 2.06 (dt, J=15.2, 7.5 Hz, 2H), 2.49 (t, J=8.1 Hz, 2H), 3.82 (t, J=7.0 Hz, 2H), 4.46 (s, 2H), 7.30-7.36 (m, J=8.5 Hz, 2H), 7.55-7.61 (m, J=8.8 Hz, 2H), 7.81-7.85 (m, J=8.5 Hz, 2H), 7.94-8.02 (m, J=8.5 Hz, 2H), 9.26 (t, J=6.1 Hz, 1H); MS (ESI+) m/z 395.0 (M+H)$^+$.

Example 11

N-{4-[(methylsulfonyl)amino]benzyl}-4-[(trifluoromethyl)thio]benzamide

The product was prepared from N-(4-(aminomethyl)phenyl)methanesulfonamide according to Method A: $^1$H NMR (500 MHz, DMSO-d$_6$) δ ppm 2.95 (s, 3H), 4.46 (s, 2H), 7.14-7.21 (m, J=8.5 Hz, 2H), 7.28-7.35 (m, J=8.5 Hz, 2H), 7.81-7.85 (m, J=8.2 Hz, 2H), 7.96-8.01 (m, J=8.5 Hz, 2H), 9.25 (t, J=6.0 Hz, 1H), 9.67 (s, 1H); MS (ESI+) m/z 405.0 (M+H)$^+$.

Example 12

N-[3-(1H-pyrazol-1-yl)benzyl]-4-[(trifluoromethyl)thio]benzamide

The product was prepared from (3-(1H-pyrazol-1-yl)phenyl)methanamine according to Method A: $^1$H NMR (500 MHz, DMSO-d$_6$) δ ppm 4.58 (s, 2H), 6.56 (dd, J=2.4, 1.8 Hz, 1H), 7.29 (d, J=7.9 Hz, 1H), 7.47 (t, J=7.8 Hz, 1H), 7.70 (dd, J=8.1, 1.4 Hz, 1H), 7.75 (d, J=1.5 Hz, 1H), 7.81 (s, 1H), 7.83-7.87 (m, J=8.2 Hz, 2H), 7.98-8.03 (m, J=8.5 Hz, 2H), 8.43 (d, J=2.4 Hz, 1H), 9.36 (t, J=5.8 Hz, 1H); MS (ESI+) m/z 378.0 (M+H)$^+$.

Example 13

N-[4-(3,5-dimethyl-1H-pyrazol-1-yl)benzyl]-4-[(trifluoromethyl)thio]benzamide

The product was prepared from (4-(3,5-dimethyl-1H-pyrazol-1-yl)phenyl)methanamine according to Method A: $^1$H NMR (500 MHz, DMSO-d$_6$) δ ppm 2.18 (s, 3H), 2.27 (s, 3H), 4.56 (s, 2H), 6.10 (s, 1H), 7.41-7.48 (m, 4H), 7.83-7.87 (m, J=8.2 Hz, 2H), 7.98-8.03 (m, J=8.2 Hz, 2H), 9.35 (t, J=6.0 Hz, 1H); MS (ESI+) m/z 406.0 (M+H)$^+$.

Example 14

N-[3-(dimethylamino)benzyl]-4-[(trifluoromethyl)thio]benzamide

The product was prepared from 3-(dimethylamino)benzylamine according to Method A: $^1$H NMR (500 MHz, DMSO-d$_6$) δ ppm 3.09 (s, 6H), 4.52 (s, 2H), 7.19 (d, J=7.6 Hz, 1H), 7.25 (d, J=8.2 Hz, 1H), 7.29 (s, 1H), 7.43 (t, J=7.8 Hz, 1H), 7.81-7.89 (m, J=8.2 Hz, 2H), 7.94-8.05 (m, J=8.5 Hz, 2H), 9.32 (t, J=5.8 Hz, 1H); MS (ESI+) m/z 355.0 (M+H)$^+$.

Example 15

N-{3-[acetyl(methyl)amino]benzyl}-4-[(trifluoromethyl)thio]benzamide

The product was prepared from N-(3-(aminomethyl)phenyl)-N-methylacetamide according to method A: $^1$H NMR (500 MHz, DMSO-d$_6$) δ ppm 1.77 (s, 3H), 3.15 (s, 3H), 4.53 (s, 2H), 7.22 (d, J=7.0 Hz, 1H), 7.27 (s, 1H), 7.32 (d, J=6.1 Hz, 1H), 7.43 (t, J=7.2 Hz, 1H), 7.81-7.86 (m, J=8.2 Hz, 2H), 7.97-8.02 (m, J=8.2 Hz, 2H), 9.31 (t, J=6.1 Hz, 1H); MS (ESI+) m/z 383.1 (M+H)$^+$.

Example 16

N-[4-(1H-pyrrol-1-yl)benzyl]-4-[(trifluoromethyl)thio]benzamide

The product was prepared from (4-(1H-pyrrol-1-yl)phenyl)methanamine according to Method A: $^1$H NMR (500 MHz, DMSO-d$_6$) δ ppm 4.51 (s, 2H), 6.27 (t, J=2.1 Hz, 2H), 7.31 (t, J=2.1 Hz, 2H), 7.40-7.44 (m, J=8.5 Hz, 2H), 7.50-7.54 (m, J=8.5 Hz, 2H), 7.82-7.86 (m, J=8.2 Hz, 2H), 7.97-8.03 (m, J=8.5 Hz, 2H), 9.31 (t, J=6.1 Hz, 1H); MS (ESI+) m/z 377.0 (M+H)$^+$.

Example 17

N-[4-(dimethylamino)benzyl]-4-[(trifluoromethyl)thio]benzamide

The product was prepared from 4-trifluoromethylthiobenzoic acid (133 mg) and 4-(dimethylamino)benzylamine dihydrochloride (134 mg) according to Method B: $^1$H NMR (300 MHz, DMSO-d$_6$) δ ppm 2.85 (s, 6H), 4.36 (d, J=5.8 Hz, 2H), 6.57-6.75 (m, J=8.8 Hz, 2H), 7.08-7.23 (m, J=8.8 Hz, 2H), 7.76-7.86 (m, J=8.5 Hz, 2H), 7.92-8.06 (m, J=8.5 Hz, 2H), 9.08 (t, J=5.8 Hz, 1H); MS (DCI/NH$_3$) m/z 355.1 (M+H)$^+$; Anal. C$_{17}$H$_{17}$F$_3$N$_2$OS: C, H, N.

Example 18

N-(4-pyrrolidin-1-ylbenzyl)-4-[(trifluoromethyl)thio]benzamide

The product was prepared from 4-trifluoromethylthiobenzoic acid (133 mg) and (4-(pyrrolidin-1-yl)phenyl)methanamine (127 mg) according to Method B: $^1$H NMR (300 MHz, DMSO-d$_6$) δ ppm 1.84-1.99 (m, 4H), 3.12-3.23 (m, 4H), 4.35 (d, J=6.1 Hz, 2H), 6.49 (m, J=8.8 Hz, 2H), 7.13 (m, J=8.8 Hz, 2H), 7.81 (m, J=8.1 Hz, 2H), 7.93-8.00 (m, 2H), 9.06 (t, J=5.9 Hz, 1H); MS (DCI/NH$_3$) m/z 381.1 (M+H)$^+$.

Example 19

N-(4-aminobenzyl)-4-[(trifluoromethyl)thio]benzamide

The product was prepared from 4-trifluoromethylthiobenzoic acid (444 mg) and 4-(aminomethyl)aniline (342 mg) according to Method B: $^1$H NMR (300 MHz, DMSO-d$_6$) δ ppm 4.30 (d, J=6.1 Hz, 2H), 4.95 (s, 2H), 6.47-6.54 (m, J=8.5 Hz, 2H), 6.93-7.02 (m, J=8.1 Hz, 2H), 7.77-7.84 (m, J=8.1 Hz, 2H), 7.93-8.02 (m, J=8.5 Hz, 2H), 9.02 (t, J=5.9 Hz, 1H); MS (ESI+) m/z 326.9 (M+H)$^+$; Anal. C$_{15}$H$_{13}$F$_3$N$_2$OS: C, H, N.

Example 20

N-[4-(methylamino)benzyl]-4-[(trifluoromethyl)thio]benzamide

The product was prepared from 4-trifluoromethylthiobenzoic acid (61 mg) and 4-(aminomethyl)-N-methylaniline (128 mg) according to Method B: $^1$H NMR (300 MHz, CDCl$_3$) δ ppm 2.84 (s, 3H) 3.76 (s, 1H) 4.52 (d, J=5.2 Hz, 2H) 6.24 (s, 1H) 6.56-6.63 (m, 2H) 7.14-7.21 (m, 2H) 7.67-7.72 (m, 2H) 7.76-7.83 (m, 2H); MS (DCI/NH$_3$) m/z 341.1 (M+H)$^+$.

Example 21

4-[(difluoromethyl)thio]-N-[4-(dimethylamino)benzyl]benzamide

A sealed tube was charged with sodium 2-chloro-2,2-difluoroacetate (0.525 g, 3.44 mmol) and sodium bicarbonate (0.284 g, 3.38 mmol) in N,N-dimethylformamide (14 mL). The vessel was purged with nitrogen, and 4-mercaptobenzoic acid (0.35 g, 2.270 mmol) was added. The mixture was warmed to 80° C. for 3 hours. After 3 hours, the reaction mixture was cooled and filtered to remove a precipitate. The N,N-dimethylformamide was diluted with 200 mL of diethyl ether and 75 mL of dichloromethane and acidified to pH 4.8 with 0.5 mL of acetic acid. The resulting cloudy solution was extracted with 3×150 mL of aqueous sodium chloride and 2×150 mL of brine. The organic layer was concentrated onto silica for loading onto a column. The product was collected after filtration through silica (40 g column, 1:1 ethyl acetate/hexane eluent). The crude product, 4-(difluoromethylthio)benzoic acid, was used as such in the next step. $^1$H NMR (300 MHz, CD$_3$OD) δ ppm 7.21 (t, J=56.3 Hz, 1H) 7.62-7.70 (AA'BB',2H) 8.00-8.08 (AA'BB',2H); MS (ESI−) m/z 202.8 (M−H)$^-$.

The product was prepared from 4-difluoromethylthiobenzoic acid (61 mg) and (4-(aminomethyl)-N,N-dimethylaniline (45 mg) according to Method B: $^1$H NMR (300 MHz, DMSO-d$_6$) δ ppm 2.85 (s, 6H), 4.36 (d, J=5.9 Hz, 2H), 6.68 (d, J=8.7 Hz, 2H), 7.14 (d, J=8.7 Hz, 2H), 7.57 (t, J=56 Hz, 1H), 7.65 (d, J=8.3 Hz, 2H), 7.92 (d, J=8.3 Hz, 2H), 9.00 (t, J=5.8 Hz, 1H); MS (DCI/NH$_3$) m/z 337.1 (M+H)$^+$; Anal. C$_{17}$H$_{18}$F$_2$N$_2$OS: C, H, N.

Example 22

4-[(difluoromethyl)thio]-N-[4-(methylamino)benzyl]benzamide

The titled compound was prepared from 4-difluoromethylthiobenzoic acid (prepared as in Example 22) (150 mg) and 4-(aminomethyl)-N-methylaniline (120 mg) according to Method B: $^1$H NMR (300 MHz, CDCl$_3$) δ ppm 2.84 (s, 3H) 4.52 (d, J=5.09 Hz, 2H) 6.60 (m, J=8.48 Hz, 2H) 6.85 (t, J=56.45 Hz, 1H) 7.18 (m, J=8.48 Hz, 2H) 7.61 (m, J=8.14 Hz, 2H) 7.71-7.83 (m, 2H); MS (DCI/NH$_3$) m/z 323 (M+H)$^+$, 340 (M+NH$_4$)$^+$.

Example 23

N-{4-[(difluoromethyl)thio]phenyl}-2-(4-pyrrolidin-1-ylphenyl)acetamide

The product was prepared from 2-(4-(pyrrolidin-1-yl)phenyl)acetic acid (133 mg) according to Method C: $^1$H NMR (300 MHz, CD$_3$OD) δ ppm 1.97-2.03 (m, 4H), 3.19-3.27 (m, 4H), 3.55 (s, 2H), 6.51-6.58 (m, 2H), 6.99 (t, J=56.7 Hz, 1H), 7.10-7.17 (m, 2H), 7.47-7.54 (m, 2H), 7.60-7.66 (m, 2H); MS (DCI/NH$_3$) m/z 363.0 (M+H)$^+$.

Example 24

N-{4-[(difluoromethyl)thio]phenyl}-2-(4-piperidin-1-ylphenyl)acetamide

The product was prepared from 2-(4-(piperidin-1-yl)phenyl)acetic acid (65 mg) according to Method C: $^1$H NMR (300 MHz, CDCl$_3$) δ ppm 1.56-1.65 (m, 2H), 1.67-1.79 (m, 4H), 3.15-3.23 (m, 4H), 3.66 (s, 2H), 6.74 (t, J=57.1 Hz, 1H), 6.94-6.98 (m, 2H), 7.13 (s, 1H), 7.15-7.20 (m, 2H), 7.40-7.52 (m, 4H); MS (DCI/NH$_3$) m/z 377.1 (M+H)$^+$.

Example 25

2-(4-azetidin-1-ylphenyl)-N-{4-[(difluoromethyl)thio]phenyl}acetamide

The product was prepared from 2-(4-(azetidin-1-yl)phenyl)acetic acid (293 mg) according to Method C: $^1$H NMR (300 MHz, CDCl$_3$) δ ppm 2.41 (dt, J=14.6, 7.3 Hz, 2H), 3.65 (s, 2H), 3.93 (t, J=7.1 Hz, 4H), 6.47-6.54 (m, 2H), 6.74 (t, J=57.1 Hz, 1H), 7.12-7.19 (m, 2H), 7.41-7.51 (m, 4H); MS (DCI/NH$_3$) m/z 349.1 (M+H)$^+$.

Example 26

2-[4-(3,3-difluoroazetidin-1-yl)phenyl]-N-{4-[(difluoromethyl)thio]phenyl}acetamide The product was prepared from 2-[4-(3,3-difluoroazetidin-1-yl)phenyl]acetic acid (133 mg) according to Method C: $^1$H NMR (300 MHz, CDCl$_3$) δ ppm 3.67 (s, 2H), 4.24 (t, J=11.7 Hz, 4H), 6.51-6.55 (m, 2H), 6.74 (t, J=57.0 Hz, 1H), 7.10 (s, 1H), 7.18-7.23 (m, 2H), 7.43-7.52 (m, 4H); MS (DCI/NH$_3$) m/z 385.0 (M+H)$^+$.

Example 27 tert-butyl 4-[2-({4-[(difluoromethyl)thio]phenyl}amino)-2-oxoethyl]phenylcarbamate The product was prepared from 2-(4-(tert-butoxycarbonylamino)phenyl)acetic acid (2.76 g) according to Method C: $^1$H NMR (300 MHz, CDCl$_3$) δ ppm 1.53 (s, 9H), 3.68-3.71 (m, 2H), 6.52 (s, 1H), 6.75 (t, J=57.0 Hz, 1H), 7.09 (s, 1H), 7.21-7.27 (m, 2H), 7.35-7.42 (m, 2H), 7.42-7.52 (m, 4H); MS (DCI/NH$_3$) m/z 426.1 (M+NH$_4$)$^+$.

Example 28

2-(4-aminophenyl)-N-{4-[(difluoromethyl)thio]phenyl}acetamide

Tert-butyl 4-[2-({4-[(difluoromethyl)thio]phenyl}amino)-2-oxoethyl]phenylcarbamate (Example 27) (3.63 g) was stirred in 25% trifluoroacetic acid/dichloromethane at room temperature for 45 minutes. The mixture was diluted with 1,2-dichloroethane (25 mL) and evaporated down twice. The residue was recrystallized from ethyl acetate (15 mL) and hexane (15 mL). The product was obtained as the 1:1 trifluoroacetate salt, 2-(4-aminophenyl)-N-(4-(difluoromethylthio)phenyl)acetamide 2,2,2-trifluoroacetate: $^1$H NMR (300

MHz, DMSO-$d_6$) δ ppm 3.45-4.13 (m, 2H) 3.62 (s, 2H) 7.03 (d, J=8.5 Hz, 2H) 7.38 (t, J=56.1 Hz, 1H) 7.28 (d, J=8.5 Hz, 2H) 7.47-7.55 (m, 2H) 7.64-7.72 (m, 2H) 10.36 (s, 1H) MS (DCI/NH$_3$) m/z 309.0 (M+H)$^+$; Anal. $C_{15}H_{14}F_2N_2OS$ $C_2HF_3O_2$: C, H, N.

Example 29

N-{4-[(difluoromethyl)thio]phenyl}-2-[4-(methylamino)phenyl]acetamide

Formic acid (0.35 mL, 9.1 mmol) was added to acetic anhydride (0.69 mL, 7.3 mmol) at 0° C. The mixture was warmed to 60° C. for 2 hours, then cooled to 0° C. To the anhydride mixture was added a solution of methyl 2-(4-aminophenyl)acetate (0.95 g, 5.7 mmol) in tetrahydrofuran (14 mL). The mixture was warmed to room temperature and stirred for 18 hours. The reaction mixture was neutralized with saturated aqueous sodium bicarbonate and diluted with ether. The ether layer was separated, dried over sodium sulfate, and concentrated. The residue was filtered through silica (1% methanol/dichloromethane eluent) to give methyl 2-(4-formamidophenyl)acetate (0.8 g, 4.14 mmol, 56% yield). The product was dissolved in tetrahydrofuran (14 mL) and cooled to 0° C. Borane methyl sulfide complex (0.393 mL, 4.14 mmol) was added. After 15 minutes, the mixture was warmed to room temperature for 30 minutes. The mixture was cooled to 0° C. again, and 5 mL of methanol was added. The mixture was concentrated and the residue was purified by silica chromatography (10% ethyl acetate/hexane eluent) to give methyl 2-(4-(methylamino) phenyl)acetate: $^1$H NMR (300 MHz, CDCl$_3$) δ ppm 2.82 (s, 3H), 3.51 (s, 2H), 3.67 (s, 3H), 6.51-6.61 (m, 2H), 6.99-7.15 (m, 2H); MS (ESI+) m/z 179.9 (M+H)$^+$.

Methyl 2-(4-(methylamino)phenyl)acetate (721 mg, 4.0 mmol) was dissolved in tetrahydrofuran (10 mL) and treated with a 1 M aqueous solution of lithium hydroxide (4.4 mmol). After 3 hours, the mixture was acidified with 1 N aqueous hydrochloric acid and concentrated to remove tetrahydrofuran. The aqueous phase was extracted with dichloromethane (2×20 mL) and the organic layer was dried and concentrated to give 2-(4-(methylamino)phenyl)acetic acid (309 mg, 1.87 mmol).

The product was prepared from 2-(4-(methylamino)phenyl)acetic acid (54 mg) according to Method C: $^1$H NMR (300 MHz, DMSO-$d_6$) δ ppm 2.64 (d, J=5.2 Hz, 3H), 3.46 (s, 2H), 5.50 (q, J=4.9 Hz, 1H), 6.43-6.53 (m, 2H), 6.99-7.09 (m, 2H), 7.37 (t, J=56.1 Hz, 1H), 7.45-7.54 (m, 2H), 7.63-7.73 (m, 2H), 10.24 (s, 1H); MS (DCI/NH$_3$) m/z 322.9 (M+H)$^+$.

Example 30

N-{4-[(difluoromethyl)thio]phenyl}-2-[4-(dimethylamino)phenyl]acetamide

The product was prepared from 2-(4-(dimethylamino)phenyl)acetic acid (54 mg) according to Method C: $^1$H NMR (300 MHz, DMSO-$d_6$) δ ppm 2.85 (s, 6H), 3.50 (s, 2H), 6.64-6.71 (m, 2H), 7.09-7.16 (m, 2H), 7.37 (t, J=56.1 Hz, 1H), 7.45-7.54 (m, 2H), 7.63-7.71 (m, 2H), 10.27 (s, 1H); MS (DCI/NH$_3$) m/z 337.1 (M+H)$^+$.

Example 31

2-[4-(dimethylamino)phenyl]-N-{4-[(trifluoromethyl)thio]phenyl}acetamide

The product was prepared from 2-(4-(dimethylamino)phenyl)acetic acid (23 mg) and 4-trifluoromethylthioaniline (28 mg) according to Method C: $^1$H NMR (300 MHz, CDCl$_3$) δ ppm 2.98 (s, 6H), 3.66 (s, 2H), 6.72-6.78 (m, 2H), 7.14-7.19 (m, 2H), 7.19 (s, 1H), 7.43-7.51 (m, 2H), 7.52-7.57 (m, 2H); MS (ESI-pos) m/z 355.0 (M+H)$^+$.

Example 32

N-{4-[(difluoromethyl)thio]phenyl}-2-[4-(isobutylamino)phenyl]acetamide

The product was prepared using isobutyraldehyde according to Method D: $^1$H NMR (500 MHz, DMSO-$d_6$) δ ppm 0.92 (d, J=6.7 Hz, 6H), 1.69-1.89 (m, 1H), 2.83 (dd, J=5.8, 6.9 Hz, 2H), 3.48 (s, 2H), 6.54-6.66 (m, 2H), 7.03-7.12 (m, 2H), 7.33 (t, J=55.8 Hz, 1H), 7.48-7.56 (m, 2H), 7.63-7.72 (m, 2H); MS (ESI+) m/z 365.0 (M+H)$^+$.

Example 33

2-{4-[(cyclohexylmethyl)amino]phenyl}-N-{4-[(difluoromethyl)thio]phenyl}acetamide The product was prepared using cyclohexanecarbaldehyde according to Method D: $^1$H NMR (500 MHz, DMSO-$d_6$) δ ppm 0.92 (m, 2H), 1.16 (m, 2H), 1.19 (m, 1H), 1.47-1.58 (m, J=18.0, 14.5, 7.0, 3.8 Hz, 1H), 1.62 (m, 1H), 1.68 (m, 2H), 1.76 (m, 2H), 2.87 (ABX, 2H), 3.49 (s, 2H), 6.63-6.69 (m, 2H), 7.07-7.13 (m, 2H), 7.33 (t, J=56.1 Hz, 1H), 7.48-7.55 (m, 2H), 7.64-7.70 (m, 2H); MS (ESI-) m/z 403.1 (M-H)$^-$.

Example 34

N-{4-[(difluoromethyl)thio]phenyl}-2-{4-[(2-methoxybenzyl)amino]phenyl}acetamide The product was prepared using 2-methoxybenzaldehyde according to Method D: $^1$H NMR (500 MHz, DMSO-$d_6$) δ ppm 3.47 (s, 2H), 3.82 (s, 3H), 4.22 (s, 2H), 6.58 (d, J=8.2 Hz, 2H), 6.88 (t, J=7.3 Hz, 1H), 6.99 (d, J=8.5 Hz, 1H), 7.03-7.09 (m, 2H), 7.20-7.24 (m, 2H), 7.33 (t, J=56.7 Hz, 1H), 7.48-7.54 (m, 2H), 7.62-7.69 (m, 2H), 10.34 (s, 1H); MS (ESI-) m/z 427.1 (M-H)$^-$.

Example 35

2-{4-[(4-chlorobenzyl)amino]phenyl}-N-{4-[(difluoromethyl)thio]phenyl}acetamide

The product was prepared using 4-chlorobenzaldehyde according to Method D: $^1$H NMR (500 MHz, DMSO-$d_6$) δ ppm 3.44 (s, 2H), 4.24 (s, 2H), 6.47-6.55 (m, 2H), 6.98-7.06 (m, 2H), 7.33 (t, J=56.0 Hz, 1H), 7.34-7.38 (m, 4H), 7.48-7.53 (m, 2H), 7.63-7.68 (m, 2H), 10.32 (s, 1H); MS (ESI-) m/z 431.0 (M-H)$^-$.

Example 36

2-{4-[(2-chlorobenzyl)amino]phenyl}-N-{4-[(difluoromethyl)thio]phenyl}acetamide

The product was prepared using 2-chlorobenzaldehyde according to Method D: $^1$H NMR (500 MHz, DMSO-$d_6$) δ ppm 3.45 (s, 2H), 4.32 (s, 2H), 6.44-6.53 (m, 2H), 7.00-7.07 (m, 2H), 7.24-7.29 (m, 2H), 7.33 (t, J=56.6 Hz, 1H), 7.38 (dd, J=6.9, 5.2, Hz, 1H), 7.44 (d, J=6.6, 2.7 Hz, 1H), 7.49-7.54 (m, 2H), 7.63-7.69 (m, 2H), 10.33 (s, 1H); MS (ESI-) m/z 431.0 (M-H)$^-$.

Example 37

N-{4-[(difluoromethyl)thio]phenyl}-2-{4-[(3-methoxybenzyl)amino]phenyl}acetamide The product was prepared using 3-methoxybenzaldehyde according to Method D: $^1$H NMR (500 MHz, DMSO-$d_6$) δ ppm 3.46 (s, 2H), 3.71 (s, 3H), 4.24 (s, 2H), 6.56-6.61 (m, 2H), 6.79 (dd, J=8.1, 2.3 Hz, 1H), 6.91 (dd, J=2.4, 1.7 Hz, 1H), 6.93 (dd, J=8.0, 1.6 Hz, 1H), 7.01-7.06 (m, 2H), 7.22 (t, J=7.6 Hz, 1H), 7.33 (t, J=56.7 Hz, 1H), 7.48-7.53 (m, 2H), 7.64-7.68 (m, 2H), 10.33 (s, 1H); MS (ESI−) m/z 427.1 (M−H)$^−$.

Example 38

N-{4-[(difluoromethyl)thio]phenyl}-2-{4-[(3-methylbutyl)amino]phenyl}acetamide

The product was prepared using 3-methylbutanal according to Method D: $^1$H NMR (500 MHz, DMSO-$d_6$) δ ppm 0.89 (d, J=6.4 Hz, 6H), 1.44 (m, 2H), 1.66 (septet, J=6.6 Hz, 1H), 3.04 (dd, J=7.8, 7.4 Hz, 2H), 3.52 (s, 2H), 6.70-6.77 (m, 2H), 7.11-7.18 (m, 2H), 7.33 (t, J=56.0 Hz, 1H), 7.50-7.54 (m, 2H), 7.64-7.69 (m, 2H), 10.37 (s, 1H); MS (ESI+) m/z 379.1 (M+H)$^+$.

Example 39

N-{4-[(difluoromethyl)thio]phenyl}-2-{4-[(quinolin-4-ylmethyl)amino]phenyl}acetamide The product was prepared as the trifluoroacetate salt using quinoline-4-carbaldehyde according to Method D: $^1$H NMR (500 MHz, DMSO-$d_6$) δ ppm 3.47 (s, 2H), 4.99 (s, 2H), 6.55-6.60 (m, 2H), 7.05-7.09 (m, 2H), 7.33 (t, J=56.0 Hz, 1H), 7.49-7.53 (m, 2H), 7.53 (m, 1H), 7.64-7.68 (m, 2H), 7.76 (d, J=5.2 Hz, 1H), 7.91 (ddd, J=8.5, 7.2, 1.1 Hz, 1H), 8.06 (ddd, J=8.4, 7.0, 1.1 Hz, 1H), 8.21 (d, J=7.9 Hz, 1H), 9.02 (d, J=5.2 Hz, 1H), 10.36 (s, 1H); MS (ESI−) m/z 448.1 (M−H)$^−$.

Example 40

N-{4-[(difluoromethyl)thio]phenyl}-2-(4-{[(5-ethyl-2-furyl)methyl]amino}phenyl)acetamide The product was prepared using 2-(5-ethylfuran-2-yl)acetaldehyde according to Method D: $^1$H NMR (500 MHz, DMSO-$d_6$) δ ppm 1.13 (t, J=7.5 Hz, 3H), 2.56 (q, J=7.6 Hz, 2H), 3.50 (s, 2H), 4.21 (s, 2H), 5.98 (d, J=3.1 Hz, 1H), 6.18 (d, J=3.1 Hz, 1H), 6.66-6.74 (m, 2H), 7.07-7.14 (m, 2H), 7.33 (t, J=56.1 Hz, 1H), 7.49-7.54 (m, 2H), 7.63-7.70 (m, 2H), 9.47 (s, 1H); MS (ESI−) m/z 415.1 (M−H)$^−$.

Example 41

N-{4-[(difluoromethyl)thio]phenyl}-2-[4-(tetrahydro-2H-pyran-4-ylamino) phenyl]acetamide The product was prepared using dihydro-2H-pyran-4(3H)-one according to Method D: $^1$H NMR (500 MHz, DMSO-$d_6$) δ ppm 1.56 (dq, J=11.7, 4.3 Hz, 2H), 1.81 (dd, J=12.5, 2.1 Hz, 2H), 3.34 (td, J=11.7, 1.5 Hz, 2H), 3.60 (tt, J=11.2, 11.2, 4.2, 4.0 Hz, 1H), 3.67 (s, 2H), 3.90 (dd, J=11.7, 2.6 Hz, 2H), 7.14-7.19 (m, 2H), 7.34 (t, J=56.2 Hz, 1H), 7.36-7.40 (m, 2H), 7.51-7.55 (m, 2H), 7.66-7.70 (m, 2H), 10.49 (s, 1H); MS (ESI−) m/z 391.1 (M−H)$^−$.

Example 42

N-{4-[(difluoromethyl)thio]phenyl}-2-{4-[(4-phenoxybenzyl)amino]phenyl}acetamide The product was prepared using 4-phenoxybenzaldehyde according to Method D: $^1$H NMR (500 MHz, DMSO-$d_6$) δ ppm 3.48 (s, 2H), 4.26 (s, 2H), 6.56-6.68 (m, 2H), 6.92-6.99 (m, 4H), 7.04-7.10 (m, 2H), 7.13 (t, J=7.5 Hz, 1H), 7.33 (t, J=56.0 Hz, 3H), 7.35-7.41 (m, 4H), 7.49-7.54 (m, 2H), 7.64-7.68 (m, 2H); MS (ESI−) m/z 489.1 (M−H)$^−$.

Example 43

2-{4-[(cyclopropylmethyl)amino]phenyl}-N-{4-[(difluoromethyl)thio]phenyl}acetamide The product was prepared using cyclopropanecarbaldehyde according to Method D: $^1$H NMR (500 MHz, DMSO-$d_6$) δ ppm 0.32 (ddd, J=6.0, 4.6, 4.4 Hz, 2H), 0.56 (ddd, J=8.1, 6.6, 4.5 Hz, 2H), 1.02 (m, 1H), 3.13 (d, J=7.3 Hz, 2H), 3.67 (s, 2H), 7.20-7.25 (m, 2H), 7.34 (t, J=56.0 Hz, 1H), 7.36-7.41 (m, 2H), 7.51-7.56 (m, 2H), 7.64-7.71 (m, 2H), 10.49 (s, 1H); MS (ESI+) m/z 363.0 (M+H)$^+$.

Example 44

2-(4-{[(4-bromothien-2-yl)methyl]amino}phenyl)-N-{4-[(difluoromethyl)thio]phenyl}acetamide The product was prepared using 4-bromothiophene-2-carbaldehyde according to Method D: $^1$H NMR (500 MHz, DMSO-$d_6$) δ ppm 3.46 (s, 2H), 4.42 (s, 2H), 6.50-6.63 (m, 2H), 7.03 (d, J=1.2 Hz, 1H), 7.03-7.07 (m, 2H), 7.33 (t, J=56.1 Hz, 1H), 7.42 (d, J=1.5 Hz, 1H), 7.49-7.54 (m, 2H), 7.64-7.69 (m, 2H), 10.34 (s, 1H); MS (ESI−) m/z 482.9 (M−H)$^−$.

Example 45

N-{4-[(difluoromethyl)thio]phenyl}-2-{4-[(quinolin-2-ylmethyl)amino]phenyl}acetamide The product was prepared as the trifluoroacetate salt using quinoline-2-carbaldehyde according to Method D: $^1$H NMR (500 MHz, DMSO-$d_6$) δ ppm 3.46 (s, 2H), 4.69 (s, 2H), 6.59-6.68 (m, 2H), 7.02-7.09 (m, 2H), 7.32 (t, J=56.0 Hz, 1H), 7.48-7.52 (m, 2H), 7.62-7.66 (m, 2H), 7.73 (m, 1H), 7.74 (d, J=8.5 Hz, 1H), 7.93 (m, 1H), 8.10 (d, J=8.2 Hz, 1H), 8.13 (m, 1H), 8.65 (d, J=8.5 Hz, 1H), 10.34 (s, 1H); MS (ESI−) m/z 448.1 (M−H)$^−$.

Example 46

2-(4-{[(1-acetyl-1H-indol-3-yl)methyl]amino}phenyl)-N-{4-[(difluoromethyl)thio]phenyl}acetamide The product was prepared using 1-acetyl-1H-indole-3-carbaldehyde according to Method D: $^1$H NMR (500 MHz, DMSO-$d_6$) δ ppm 2.61 (s, 3H), 3.48 (s, 2H), 4.40 (s, 2H), 6.68-6.78 (m, 2H), 7.06-7.14 (m, 2H), 7.28 (t, J=7.5 Hz, 1H), 7.33 (t, J=56.4 Hz, 1H), 7.34 (t, J=7.6 Hz, 1H), 7.47-7.54 (m, 2H), 7.63-7.70 (m, 2H), 7.72 (d, J=7.6 Hz, 1H), 7.80 (s, 1H), 8.30 (d, J=8.2 Hz, 1H); MS (ESI−) m/z 478.1 (M−H)$^−$.

Example 47

2-[4-(cyclohexylamino)phenyl]-N-{4-[(difluoromethyl)thio]phenyl}acetamide

The product was prepared using cyclohexanone according to Method D: $^1$H NMR (500 MHz, DMSO-d$_6$) δ ppm 1.13 (qt, J=12.3, 2.1 Hz, 1H), 1.25 (qt, J=12.8, 2.8 Hz, 2H), 1.32 (m, 2H), 1.60 (dt, J=12.8, 2.0 Hz, 1H), 1.75 (dt, J=12.8, 2.2 Hz, 2H), 1.88 (ddd, J=11.0, 3.5, 1.9 Hz, 2H), 3.35 (tt, J=10.8, 3.5 Hz, 1H), 3.71 (s, 2H), 7.26-7.32 (m, 2H), 7.34 (t, J=56.0 Hz, 1H), 7.39-7.48 (m, 2H), 7.48-7.57 (m, 2H), 7.63-7.74 (m, 2H), 10.52 (s, 1H); MS (ESI−) m/z 389.1 (M−H)⁻.

Example 48

2-[4-({[5-(2-chlorophenyl)-2-furyl]methyl}amino)phenyl]-N-{4-[(difluoromethyl)thio]phenyl}acetamide The product was prepared using 5-(2-chlorophenyl)furan-2-carbaldehyde according to Method D: $^1$H NMR (500 MHz, DMSO-d$_6$) δ ppm 3.48 (s, 2H), 4.32 (s, 2H), 6.45 (d, J=3.4 Hz, 1H), 6.65-6.69 (m, 2H), 7.05 (d, J=3.4 Hz, 1H), 7.06-7.11 (m, 2H), 7.30 (td, J=7.7, 1.7 Hz, 1H), 7.33 (t, J=56.0 Hz, 1H), 7.41 (td, J=7.6, 1.2 Hz, 1H), 7.50-7.54 (m, 2H), 7.52 (m, 1H), 7.65-7.69 (m, 2H), 7.80 (dd, J=7.9, 1.5 Hz, 1H), 10.34 (s, 1H); MS (ESI−) m/z 497.1 (M−H)⁻.

Example 49

N-{4-[(difluoromethyl)thio]phenyl}-2-{4-[(4-methoxybenzyl)amino]phenyl}acetamide The product was prepared using 4-methoxybenzaldehyde according to Method D: $^1$H NMR (500 MHz, DMSO-d$_6$) δ ppm 3.45 (s, 2H), 3.71 (s, 3H), 4.18 (s, 2H), 6.53-6.61 (m, 2H), 6.78-6.93 (m, 2H), 6.98-7.09 (m, 2H), 7.25-7.30 (m, 2H), 7.33 (t, J=56.0 Hz, 1H), 7.47-7.56 (m, 2H), 7.60-7.72 (m, 2H), 10.33 (s, 1H); MS (ESI−) m/z 427.1 (M−H)⁻.

Example 50

2-[4-(cyclopentylamino)phenyl]-N-{4-[(difluoromethyl)thio]phenyl}acetamide

The product was prepared using cyclopentanone according to Method D: $^1$H NMR (500 MHz, DMSO-d$_6$) δ ppm 1.52-1.65 (m, 4H), 1.72-1.75 (m, 2H), 1.83-1.94 (m, 2H), 3.69 (s, 2H), 3.85 (pentet, J=7.0 Hz, 1H), 7.20-7.27 (m, 2H), 7.34 (t, J=56.0 Hz, 1H), 7.39-7.43 (m, 2H), 7.49-7.60 (m, 2H), 7.65-7.72 (m, 2H), 10.51 (s, 1H); MS (ESI+) m/z 377.2 (M+H)⁺.

Example 51

2-{4-[(3-chlorobenzyl)amino]phenyl}-N-{4-[(difluoromethyl)thio]phenyl}acetamide

The product was prepared using 3-chlorobenzaldehyde according to Method D: $^1$H NMR (500 MHz, DMSO-d$_6$) δ ppm 3.45 (s, 2H), 4.27 (s, 2H), 6.44-6.59 (m, 2H), 6.98-7.09 (m, 2H), 7.27 (ddd, J=7.5, 1.8, 1.7 Hz, 1H), 7.31 (ddd, J=7.5, 1.8, 1.7 Hz, 1H), 7.33 (t, J=56.1 Hz, 1H), 7.34 (t, J=7.7 Hz, 1H), 7.38 (dd, J=1.9, 1.7 Hz, 1H), 7.47-7.58 (m, 2H), 7.62-7.71 (m, 2H); MS (ESI−) m/z 431.0 (M−H)⁻.

Example 52

2-[4-(cyclobutylamino)phenyl]-N-{4-[(difluoromethyl)thio]phenyl}acetamide

The product was prepared using cyclobutanone according to Method D: $^1$H NMR (500 MHz, DMSO-d$_6$) δ ppm 1.77 (m, 2H), 2.04 (m, 2H), 2.22 (m, 2H), 3.62 (s, 2H), 3.94 (dt, J=15.6, 7.9 Hz, 1H), 6.97-7.04 (m, 2H), 7.34 (t, J=56.0 Hz, 1H), 7.29-7.33 (m, 2H), 7.50-7.57 (m, 2H), 7.65-7.73 (m, 2H), 10.46 (s, 1H); MS (ESI−) m/z 361.1 (M−H)⁻.

Example 53

2-[4-(cycloheptylamino)phenyl]-N-{4-[(difluoromethyl)thio]phenyl}acetamide

The product was prepared using cycloheptanone according to Method D: $^1$H NMR (500 MHz, DMSO-d$_6$) δ ppm 1.41 (m, 2H), 1.46-1.60 (m, 6H), 1.68 (m, 2H), 1.91 (m, 2H), 3.55 (ddd, J=13.9, 9.5, 4.1 Hz, 1H), 3.71 (s, 2H), 7.25-7.32 (m, 2H), 7.34 (s, 1H), 7.41-7.48 (m, 2H), 7.51-7.57 (m, 2H), 7.66-7.72 (m, 2H); MS (ESI−) m/z 403.1 (M−H)⁻.

Example 54

N-{4-[(difluoromethyl)thio]phenyl}-2-{4-[(2-methylbutyl)amino]phenyl}acetamide

The product was prepared using 2-methylbutanal according to Method D: $^1$H NMR (500 MHz, DMSO-d$_6$) δ ppm 0.87 (t, J=7.5 Hz, 3H), 0.93 (d, J=6.7 Hz, 3H), 1.16 (dqd, J=7.6, 7.5, 6.3, 1H), 1.41-1.51 (dqd, J=7.6, 7.5, 6.0, 1H), 1.65 (ddqdd, J=7.3, 7.2, 6.7, 6.3, 6.0 Hz, 1H), 2.89 (dd, J=12.5, 7.3 Hz, 1H), 3.02 (dd, J=12.7, 6.3 Hz, 1H), 3.55 (s, 2H), 6.80-6.89 (m, 2H), 7.18-7.22 (m, 2H), 7.33 (t, J=56.0 Hz, 1H), 7.50-7.55 (m, 2H), 7.62-7.71 (m, 2H), 10.40 (s, 1H); MS (ESI+) m/z 379.0 (M+H)⁺.

Example 55

N-{4-[(difluoromethyl)thio]phenyl}-2-(4-{[(5-methylthien-2-yl)methyl]amino}phenyl)acetamide The product was prepared using 5-methylthiophene-2-carbaldehyde according to Method D: $^1$H NMR (500 MHz, DMSO-d$_6$) δ ppm 2.35 (s, 3H), 3.46 (s, 2H), 4.34 (s, 2H), 6.59-6.62 (m, 2H), 6.61 (d, J=3.4 Hz, 1H), 6.80 (d, J=3.4 Hz, 1H), 7.02-7.08 (m, 2H), 7.33 (t, J=56.0 Hz, 1H), 7.48-7.55 (m, 2H), 7.63-7.71 (m, 2H); MS (ESI−) m/z 417.0 (M−H)⁻.

Example 56

N-{4-[(difluoromethyl)thio]phenyl}-2-{4-[(2-naphthylmethyl)amino]phenyl}acetamide The product was prepared using 2-naphthaldehyde according to Method D: $^1$H NMR (500 MHz, DMSO-d$_6$) δ ppm 3.45 (s, 2H), 4.44 (s, 2H), 6.60-6.67 (m, 2H), 7.01-7.08 (m, 2H), 7.32 (t, J=56.0 Hz, 1H), 7.46-7.49 (m, 2H), 7.49-7.52 (m, 2H), 7.53 (dd, J=6.5, 1.5 Hz, 1H), 7.62-7.67 (m, 2H), 7.84 (dd, J=5.3, 4.4 Hz, 1H), 7.86-7.89 (m, 2H), 10.32 (s, 1H); MS (ESI−) m/z 447.1 (M−H)⁻.

Example 57

N-{4-[(difluoromethyl)thio]phenyl}-2-{4-[(3,3,5,5-tetramethylcyclohexyl)amino]phenyl}acetamide The product was prepared using 3,3,5,5-tetramethylcyclohexanone according to Method D: $^1$H NMR (500 MHz, DMSO-$d_6$) δ ppm 0.91 (s, 6H), 0.99 (s, 6H), 1.08 (d, J=14.0 Hz, 1H), 1.13 (t, J=12.2 Hz, 2H), 1.27 (d, J=13.7 Hz, 1H), 1.65 (d, J=11.6 Hz, 2H), 3.67 (tt, J=11.9, 3.4 Hz, 1H), 3.70 (s, 2H), 7.34 (t, J=56.0 Hz, 1H), 7.24-7.30 (m, 2H), 7.40-7.44 (m, 2H), 7.50-7.56 (m, 2H), 7.67-7.71 (m, 2H), 10.52 (s, 1H); MS (ESI+) m/z 447.1 (M+H)$^+$.

Example 58

N-{4-[(difluoromethyl)thio]phenyl}-2-{4-[(thien-2-ylmethyl)amino]phenyl}acetamide The product was prepared using thiophene-2-carbaldehyde according to Method D: $^1$H NMR (500 MHz, DMSO-$d_6$) δ ppm 3.46 (s, 2H), 4.43 (s, 2H), 6.56-6.66 (m, 2H), 6.96 (dd, J=5.0, 3.5 Hz, 1H), 7.03 (dd, J=3.4, 0.9 Hz, 1H), 7.33 (dd, J=5.2, 1.2 Hz, 1H), 7.33 (t, J=56.0 Hz, 1H), 7.47-7.57 (m, 2H), 7.62-7.70 (m, 2H); MS (ESI−) m/z 403.0 (M−H)$^-$.

Example 59

N-{4-[(difluoromethyl)thio]phenyl}-2-[4-(neopentylamino)phenyl]acetamide

The product was prepared using pivalaldehyde according to Method D: $^1$H NMR (500 MHz, DMSO-$d_6$) δ ppm 0.97 (s, 9H), 2.88 (s, 2H), 3.53 (s, 2H), 6.79-6.88 (m, 2H), 7.10-7.19 (m, 2H), 7.33 (t, J=56.0 Hz, 1H), 7.48-7.57 (m, 2H), 7.63-7.73 (m, 2H), 10.38 (s, 1H); MS (ESI+) m/z 379.0 (M+H)$^+$.

Example 60

N-{4-[(difluoromethyl)thio]phenyl}-2-(4-{[4-(trifluoromethyl)cyclohexyl]amino}phenyl)acetamide The product was prepared using 4-(trifluoromethyl)cyclohexanone according to Method D: $^1$H NMR (500 MHz, DMSO-$d_6$) δ ppm 1.30-1.42 (m, 4H), 1.94 (m, 2H), 2.00 (m, 2H), 2.27 (m, 1H), 3.37 (m, 1H), 3.64 (s, 2H), 7.05-7.14 (m, 2H), 7.34 (t, J=56.0 Hz, 1H), 7.32-7.38 (m, 2H), 7.50-7.56 (m, 2H), 7.64-7.71 (m, 2H); MS (ESI+) m/z 459.1 (M+H)$^+$.

Example 61

N-{4-[(difluoromethyl)thio]phenyl}-2-{4-[(2,2,2-trifluoroethyl)amino]phenyl}acetamide The product was prepared using trifluoroacetaldehyde according to Method D: $^1$H NMR (500 MHz, DMS-$d_6$) δ ppm 3.49 (s, 2H), 3.86 (q, J=9.7 Hz, 2H), 6.65-6.71 (m, 2H), 7.06-7.12 (m, 2H), 7.33 (t, J=56.0 Hz, 1H), 7.50-7.54 (m, 2H), 7.63-7.70 (m, 2H), 10.36 (s, 1H); MS (ESI−) m/z 389.0 (M−H)$^-$.

Example 62

N-{4-[(difluoromethyl)thio]phenyl}-2-{4-[(3-phenylcyclohexyl)amino]phenyl}acetamide The product was prepared using 3-phenylcyclohexanone according to Method D: $^1$H NMR (500 MHz, DMSO-$d_6$) δ ppm 1.55 (qd, J=11.9, 2.1 Hz, 1H), 1.59-1.69 (m, 2H), 1.72-1.92 (m, 6H), 2.99 (tt, J=11.1, 2.1 Hz, 1H), 3.60 (s, 2H), 7.00-7.07 (m, 2H), 7.19 (t, J=7.3 Hz, 1H), 7.21-7.26 (m, 2H), 7.26-7.33 (m, 4H), 7.33 (t, J=56.0 Hz, 1H), 7.49-7.56 (m, 2H), 7.64-7.70 (m, 2H); MS (ESI−) m/z 465.2 (M−H)$^-$.

DETERMINATION OF BIOLOGICAL ACTIVITY

To determine the effectiveness as allosteric modulators, the compounds of the invention were evaluated according to the following assays using *Xenopus* oocytes, cells or cell lines expressing endogenous or recombinant α7 NNRs.

The assays include (i) *Xenopus* oocytes injected with α7 NNR cRNA or cDNA and evaluation of compound effects on current responses evoked by acetylcholine or another agonist (ii) IMR-32 cells endogenously expressing α7 NNRs and measuring Ca$^{2+}$ flux or membrane potential changes utilizing the fluorescence-imaging plate reader (FLIPR)-based assays and (iii) measurement of phospho-ERK activity using western blot assays.

To determine the effectiveness of compounds of formula (I) in reducing pain, the compounds of the invention were evaluated in the formalin-induced persistent nociceptive behavior assay.

A sensory gating (N40) assay in DBA/2 mice was used to determine whether or not compounds of the invention enhance the ability of the test animals to focus on important stimuli and ignore irrelevant background noise.

Binding to sigma receptors (σ1 and σ2) were used as a selectivity assay.

(i) Two-Electrode Voltage-Clamp in *Xenopus laevis* Oocytes

*X. laevis* oocytes were prepared for electrophysiological experiments as described in the literature (see for example, Briggs, C. A. et al, *Neuropharmacology*, 1995, 34: 583-590; Briggs, C. A. et al., *Neuropharmacology*, 1998, 37: 1095-1102, which are incorporated herein by reference). In brief, three to four lobes from ovaries of female adult *X. laevis* frogs were removed and defolliculated after treatment with collagenase type 1A (2 mg/mL; Sigma) prepared in low-Ca$^{2+}$ Barth's solution (90 mM NaCl, 1.0 mM KCl, 0.66 mM NaNO$_3$, 2.4 mM NaHCO$_3$, 10 mM HEPES, 2.5 mM sodium pyruvate, 0.82 mM MgCl$_2$, and 0.5% (v/v) penicillin-streptomycin solution, pH=7.55, Sigma) for about 1.5 hours to about 2 hours at about 18° C. under constant agitation to obtain isolated oocytes.

The isolated oocytes were injected with about 4 ng to about 6 ng of human α7 NNR cRNA, kept at about 18° C. in a humidified incubator in modified Barth's solution (90 mM NaCl, 1.0 mM KCl, 0.66 mM NaNO$_3$, 2.4 mM NaHCO$_3$, 10 mM HEPES, 2.5 mM sodium pyruvate, 0.74 mM CaCl$_2$, 0.82 mM MgCl$_2$, 0.5% (v/v) penicillin-streptomycin solution, pH 7.55) and used about 2 to 7 days after injection. Responses were measured by two-electrode voltage clamp using a Parallel Oocyte Electrophysiology Test Station (Abbott, Abbott Park, Ill.) (see for example, Trumbull, J. D., et al., *Receptors Channels*, 2003, 9: 19-28, which is incorporated herein by reference). During recordings, the oocytes were bathed in Ba$^{2+}$—OR2 solution (90 mM NaCl, 2.5 mM KCl, 2.5 mM BaCl$_2$, 1.0 mM MgCl$_2$, 5.0 mM HEPES, and 0.0005 mM atropine, pH 7.4) to prevent activation of Ca$^{2+}$-dependent currents and held at −60 mV at room temperature (about 20° C.). Test compounds were pre-applied alone for ~60 seconds and subsequently in the presence of 0.1 mM acetylcholine (ACh) as the agonist. The data were expressed as percentage potentiation of the acetylcholine-evoked current normalized to the response of reference PAM (at 10 μM, N'-[(2Z)-3-(2,2-difluoro-1,3-benzodioxol-5-yl)-5-methyl-1,3-thiazol-2

(3H)-ylidene]-N,N-dimethylurea) taken as 100% and the response to submaximum ACh without any PAM as 0%.

Figure 2:
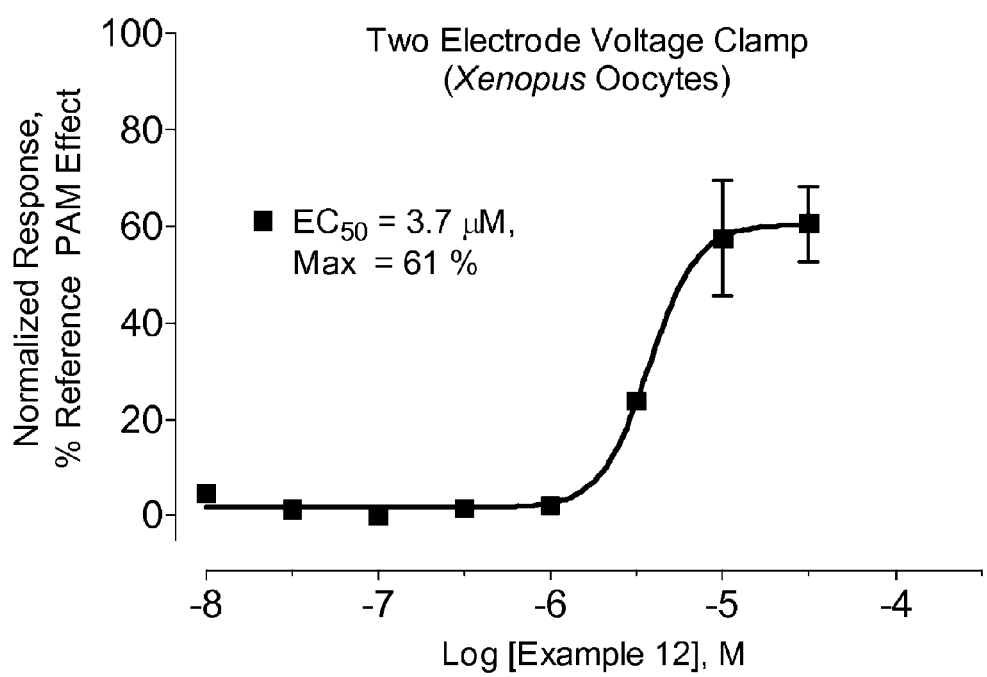
FIG. 2 is a concentration response curve obtained in the same manner for a PAM (Example 12). The response obtained by submaximum ACh in the presence of the reference PAM at 10 μM (N'-[(2Z)-3-(2,2-difluoro-1,3-benzodioxol-5-yl)-5-methyl-1,3-thiazol-2(3H)-ylidene]-N,N-dimethylurea) is considered as 100% and the response of submaximum ACh without any PAM as 0%. Normalized PAM potentiation is plotted on the Y-axis as a function of the concentration of the test modulator (depicted along the X-axis).

FIG. 1 shows the concentration-response relationship for Example 17 in potentiating 0.1 mM ACh-evoked α7 currents in oocytes. In this graph, the $EC_{50}$ value is 0.18 µM and the degree of normalized potentiation is 94%. FIG. 2 shows the concentration-response relationship for Example 12 in potentiating 0.1 mM ACh-evoked α7 currents in oocytes. In this graph, the $EC_{50}$ value is 3.7 µM and the degree of potentiation is 61%.

(ii) High-Throughput Calcium Flux Assays Using Cells Expressing Endogenous α7 NNRs Since allosteric modulators affect the kinetics of channel function and thus affect calcium dynamics, it is demonstrated that novel modulators can be identified when assays are conducted in the presence of a selective agonist, and conversely, novel agonists can be identified when screened or tested in the presence an allosteric modulator. As such, PAMs and NNR agonists can be identified by using IMR-32 cells that endogenously express various nicotinic receptors including α7 NNRs. It is contemplated that such an assay can be utilized with a number of cell lines that express α7 NNR subunits, and conventionally not amenable to α7 nicotinic compound screening. Accordingly, allosteric modulator compounds described herein can be identified using a fluorescence-based throughput functional assay using cell lines such as IMR-32 neuroblastoma or primary dissociated neurons.

Although cell types such as IMR-32 neuroblastoma and neurons are known to contain several nicotinic receptor subunits, α7 selective agonists in the present assay selectively stimulate calcium responses only in the presence of PAMs. Any suitable selective α7 agonist can be used. Selective α7 agonists from a range of structural types may be used such as those described in the literature including PNU-282987, SSR180711A and AR-R17779, and others described in earlier patent applications, such as 2-methyl-5-(6-phenyl-pyridazin-3-yl)-octahydro-pyrrolo[3,4-c]pyrrole (see for example, US 20050065178), 5-[6-(5-methyl-hexahydro-pyrrolo[3,4-c]pyrrol-2-yl)-pyridazin-3-yl]-1H-indole (see for example, US 20050065178), 3-[6-(1H-indol-5-yl)-pyradazin-3-yloxy]-1-aza-bicyclo[2.2.2]octane (see for example, US 2005/0137204 and US 2005/0245531), and 4-(5-phenyl-[1,3,4]oxadiazol-2-yl)-1,4-diaza-bicyclo[3.2.2]nonane (see for example, WO 2004/029053).

IMR-32 neuroblastoma cells (ATCC) were grown to confluency in 162 cm² tissue culture flasks in minimum essential media supplemented with 10% fetal bovine serum and 1 mM sodium pyruvate, 0.1 mM non-essential amino acids and 1% antibiotic-antimycotic. The cells were then dissociated using cell dissociation buffer and 100 µL of $3.5 \times 10^5$ cells/mL cell suspension was plated (about 75,000-100,000 cells/well) into black 96 well plates precoated with poly-D-lysine with a clear bottom and maintained for 24-48 hours in a tissue culture incubator at 37° C. under an atmosphere of 5% $CO_2$: 95% air. Other clonal cell lines or dissociated primary cortical neurons that express endogenous α7 nicotinic receptors may also be used in this assay.

Calcium flux was measured using a calcium-3 assay kit (Molecular Devices, Sunnyvale, Calif.) or Fluo-4 (Invitrogen, Carlsbad, Calif.). A stock solution of the dye was prepared by dissolving each vial supplied by the vendor in Hank's balanced salt solution buffer (HBSS) containing 10 or 20 mM HEPES. The stock solution was diluted 1:20 using the same buffer before use. The growth media was removed from the cells and loaded with 100 µL of the dye and incubated at room temperature for one to three hours. Fluorescence measurements were read simultaneously from all the wells by a Fluorometric Imaging Plate Reader (FLIPR) at an excitation wavelength of 480 nm and an emission wavelength of 520 nm. Baseline fluorescence was measured for the first 10 seconds at which 50 µL of 3× concentrations of modulator/test compounds were added to the cell plate and incubated for three to five minutes. The fluorescence intensity was captured every second for the first 1 minute followed by every 2-5 seconds for an additional two to four minutes. This procedure was followed by 50 µL of 4× concentration of agonist and readings were taken for a period of three to five minutes as described above.

The assay can also be adapted to other formats such as 384- or 1536-well formats. The concentration dependence of changes in fluorescence responses was fitted by nonlinear regression analysis (GraphPad Prism, San Diego, Calif.) or Assay Explorer (Elsevier MDL, San Ramon, Calif.) to obtain $EC_{50}$ values. Agonist alone did not evoke any responses. However, in the presence of an allosteric modulator, the agonist elicited a concentration dependent increase in calcium response. The α7 NNR selective antagonist, methyllycaconitine (MLA), abolished the response demonstrating that the effects are mediated via α7 NNR.

PAMs were identified by measuring fluorescence changes to intracellular calcium in a fluorometric plate reader in the presence of a selective α7 NNR agonist using cells natively expressing α7 NNRs. Compounds with PAM activity evoked a calcium fluorescence response in the IMR-32 neuroblastoma cell line, a cell line that expresses endogenous α7 NNRs when the assay is conducted in presence of an α7 NNR agonist. The agonist alone did not evoke a calcium response. However, when the agonist and the modulator were co-applied together, calcium responses were triggered. In the example above, 4-(5-phenyl-[1,3,4]oxadiazol-2-yl)-1,4-diaza-bicyclo[3.2.2]nonane (see for example, WO 2004/029053) was used as an agonist at 1 µM in the presence of varying concentrations of compounds of the invention. The $EC_{50}$ values of PAM compounds as determined in this assay typically can range from 1 nM to >30 µM. Other α7 NNR agonists including 2-methyl-5-(6-phenyl-pyridazin-3-yl)-octahydro-pyrrolo[3,4-c]pyrrole (published in US 20050065178), 5-[6-(5-methyl-hexahydro-pyrrolo[3,4-c]pyrrol-2-yl)-pyridazin-3-yl]-1H-indole (published in US 20050065178), various quinuclidine derivatives (see for example, US 2005/0137204 and US 2005/0245531) and PNU-282987 (see for example, Hajos, M., et al., *J Pharmacol. Exp Ther.*, 2005, 312: 1213-22) also are suitable for the assay. Likewise, primary neurons and other clonal cell lines that natively express α7 NNRs may also be utilized. Other fluorescence measurements such as those monitoring changes in membrane potential also are suitable for the assay.

(iii) High-Throughput ERK Phosphorylation Assays Using Cells Expressing Endogenous α7 NNRs Rat pheochromocytoma (PC-12) cells (ATCC, Manassas, Va.) were cultured and maintained in F-12K media supplemented with 15% horse serum, 2.5% fetal calf serum, and 2 mM L-glutamine in poly-D lysine coated dishes at 37° C. and 5% $CO_2$. Cells were plated in black-walled clear bottom 96-well Biocoat™ plates coated with poly-D-lysine (BD Biosciences, Bedford, Mass.) and grown for 2-3 days. Afterward, the culture media is replaced with serum-free media to starve cells overnight. On the day of the assay, cell media was removed and cells (60-80% confluent) were treated with agonist and/or modulator in Dulbecco's phosphate buffer saline (D-PBS) (with $Ca^{2+}$, $Mg^{2+}$, and 1 mg/mL D-glucose), as indicated in the result section.

PC-12 cells are treated for 10 minutes at 37° C. with test PAM compounds and then challenged with a selective α7

NNR agonist for 5 minutes at 37° C. in a final volume of 100 μL/well, unless otherwise indicated. After treatment, media was discarded and adherent cells were immediately fixed in the presence of 150 μL/well of 3.7% formaldehyde/phosphate-buffered saline for 30-60 minutes at room temperature. Cells were then washed (4 times/5 minutes) and permeabilized with 200 μL/well of 0.1% Triton X-100/PBS. Permeabilized cells were blocked using the Odyssey® blocking buffer (100 μL/well) and plates were rocked overnight at 4° C. Both anti-total ERK (rabbit) and anti-phospho ERK (mouse) antibodies were diluted to 1/1000 and 1/500, respectively, in Odyssey® blocking buffer and added together at 50 μL/well for 2-3 hours at room temperature. Polyclonal rabbit anti-ERK1/2 and monoclonal mouse anti-phospho-ERK 1/2 were purchased from Sigma-Aldrich (St. Louis, Mo.). The plates were washed 4 times with 0.1% Tween 20/PBS (200 uL/well), and incubated with secondary antibodies (1/1000 dilution) in blocking buffer supplemented with 0.2% Tween for 1 hour. Alexa Fluor® 680-labeled goat anti-rabbit antibodies were added to recognize total ERK labeling (red color) and IRDye™800-labeled donkey anti-mouse antibodies were added to recognize phospho-ERK labeling (green color). Alexa Fluor® 680-labeled goat-anti-rabbit antibodies were obtained from Molecular Probes (Eugene, Oreg.). IRDye™ 800CW-labeled donkey-anti-mouse antibodies were purchased from Rockland (Gilbertsville, Pa.). The plates were washed 4 times with 0.2% Tween and 0.01% SDS/PBS and scanned using the Odyssey® infrared scanner. Well intensities were quantitated and phospho-ERK signals were normalized to total ERK signals by the Odyssey® software. Data analysis was performed using GraphPad Prism (GraphPad Software, San Diego, Calif.).

PAMs can be identified by measuring changes in the phosphorylation of ERK (extracellular receptor kinase) by in-cell western analysis. Compounds with allosteric modulator activity evoke concentration-dependent increases in ERK phosphorylation. To obtain data, an α7 NNR agonist such as PNU-282987 (see for example, Hajos et al. *J Pharmacol. Exp Ther.* 2005; 312: 1213-22) was used as the α7 selective agonist. Typical $EC_{50}$ values in this assay range from about 10 nM to about 30 μM. Other α7 nicotinic receptor agonists including 2-methyl-5-(6-phenyl-pyridazin-3-yl)-octahydro-pyrrolo[3,4-c]pyrrole, 5-[6-(5-methyl-hexahydro-pyrrolo[3,4-c]pyrrol-2-yl)-pyridazin-3-yl]-1H-indole (published in US 20050065178), various quinuclidine derivatives (see for example, US 2005/0137204 and US 2005/0245531) and 4-(5-phenyl-[1,3,4]oxadiazol-2-yl)-1,4-diaza-bicyclo[3.2.2]nonane and related analogs (see for example, WO 2004/029053) also are suitable for the assay.

(iv) Formalin-Induced Persistent Nociceptive Behavior Assay

Nociception was assessed using the formalin test. The mice were placed in open plexiglass observation chambers for 30 minutes to allow them to acclimate to their surroundings; then they were removed for formalin administration. Mice were gently restrained while the dorsum of the hind paw was injected with 20 μL of 2.5% formalin into the plantar surface of the right hind paw with a 30-gauge needle. The animals were returned to the chambers and nociceptive behavior was observed immediately after formalin injection. Mirrors were placed in each chamber to enable unhindered observation. Nociceptive behavior was quantified as the time licking the injected paw for continuous 5 minutes (phase 1) and 20-45 minutes (phase 2), following formalin injection. Formalin-induced flinching/licking behavior was biphasic. The initial acute phase (phase 1, 0-5 minutes) was followed by a relatively short quiescent period, which was then followed by a prolonged tonic response (phase 2, 20-45 minutes).

Figure 3:
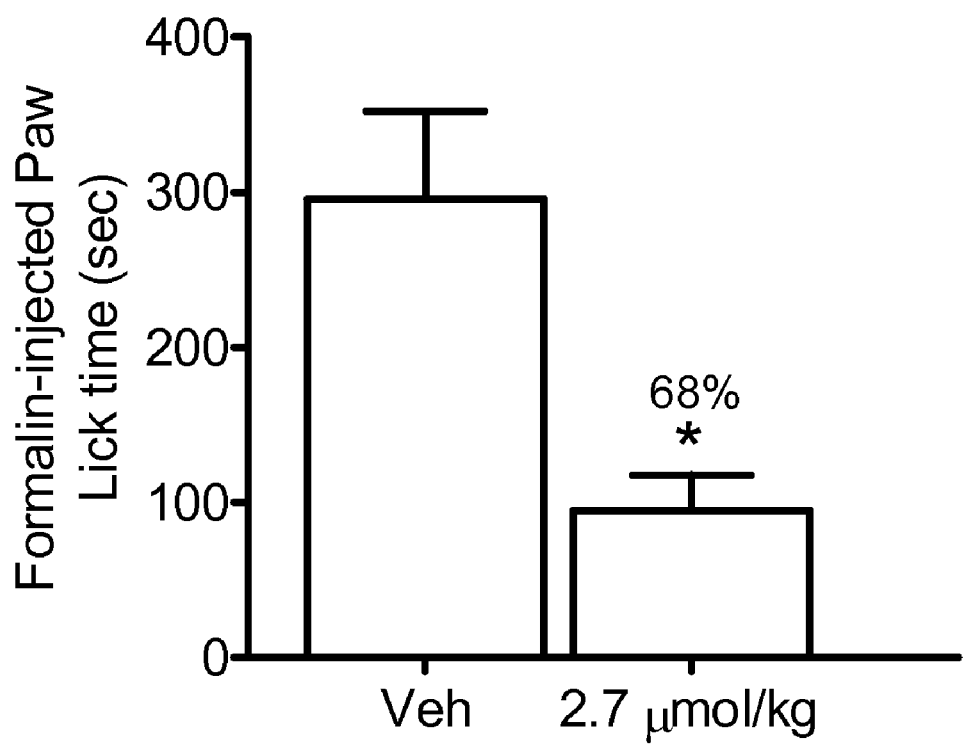
FIG. 3 is a graphical representation of nocifensive response (licking duration) following treatment with vehicle or a PAM (Example 20) followed by exposure to formalin in mice. In Phase 2 (20-45 minutes post formalin injection) a significant reduction (68%) in licking behavior was observed, indicative of pain relief in this time period.

A reference PAM compound (N-[4-(methylamino)benzyl]-4-[(trifluoromethyl)thio]benzamide (Example 20) at 10 mg/kg in 10% DMSO/HBC) administered subcutaneously 10 minutes prior to formalin injection reduced nociceptive behaviors of injected paw flicking duration in phase 2 by 68%, indicative of pain relief in this time period as shown in FIG. 3 indicating that the PAM compound might have inhibitory effect on formalin-induced central neuronal sensitization.

(v) Sensory Gating Deficit in DBA/2 mice (N40 Gating) Assay

Sensory gating is a basic central nervous system function that facilitates attending to important stimuli, and ignoring irrelevant background noise. A practical example of sensory gating is the ability to follow a conversation at a loud party. An experimental measure of sensory gating is the suppression of brainwave (evoked potential) responding to repetitive auditory stimuli. Schizophrenic patients can not suppress responding to repetitive stimuli, and are therefore considered to have sensory gating deficiencies. The DBA/2 mouse is a strain that shows a similar inability to suppress N40 evoked potential responding to repetitive auditory stimuli.

DBA/2 mice (20-25 g, 8-10 week, Harlan) were used for gating experiments and handled in accordance with approved Association for Assessment and Accreditation of Laboratory Animal Care procedures. Mice were given food and water ad libitum and maintained on a 12-hour light/dark cycle (lights on at 0600 hours).

The surgical techniques employed were similar to those previously described (Connolly P M, et al. (2003) Brain Res 992(1):85-95). The mice were stereotaxically implanted with tripolar stainless steel wire electrodes (Plastics One, Roanoke, Va., USA) for Electorencephalogram (EEG) recordings in the CA3 region of the hippocampus. The mice were first anesthetized with a solution of 2.8% ketamine (Fort Dodge Animal Health, Overland Park, Kans., USA), 0.28% xylazine (Phoenix Pharmaceuticals St. Joseph, Mo., USA), and 0.05% acepromazine (Phoenix Pharmaceuticals St. Joseph, Mo., USA) at 140 mg/kg of ketamine. A scalp incision was made along the centerline, and the exposed skull was disinfected and dried with 3.0% hydrogen peroxide. Three drill holes (#68 drill bit) were made at mediolateral (ML) 1.0, 1.8, and 2.6 mm from the central suture. All three holes were located at anteroposterior (AP)-1.8 mm from the bregma; thus, the holes were in a plane perpendicular to the central suture. The hole at ML 2.6 and AP-1.8 mm was for the electrode directed at the hippocampus. The holes at ML 1.0, AP-1.8 mm and ML 1.8, AP-1.8 mm were for cortical and reference electrodes, respectively. The depth of the hippocampal electrode tip was dorsoventral (DV) 1.65-1.70 mm below the surface of the cortex. The depth of the cortical and reference electrodes was DV 0.5 mm from the surface of the skull, a distance that resulted in the electrode being in contact with, but not penetrating, the cortical tissue. Two additional holes were drilled in the contralateral skull for placement of anchoring screws (#00-90, 1/16"). These screws were then driven into the skull, followed by the lowering of the tripolar electrode into the brain with a stereotaxic electrode holder. Before completely inserting the electrodes, a drop of cyanoacrylic glue was placed on the skull underneath the electrode pedestal. The electrodes and the pedestal were then completely lowered and the glue was allowed to dry for several minutes. The pedestal was permanently affixed to the skull with dental acrylic. The mice were then allowed to recover for at least 4 days before conducting experiments.

To obtain EEG and evoked potentials (EPs), unanesthetized mice were recorded in acoustically isolated chambers (Med Associates). EEG biosignals were recorded from freely moving mice using flexible cable tethers and electrical swivels (Plastics One) and amplified with differential AC amplifiers (Grass Instrument Division, Astro-Med, West Warwick, R.I., USA). The EEG was amplified by a factor of 1,000, and band pass filters were set at 1 and 300 Hz. Auditory EPs were generated by the presentation of 120 sets of paired white noise bursts (5 ms durations) from a speaker within the recording chamber at a distance of approximately 15-20 cm from the mouse. The first auditory stimulus of the pair, or the conditioning stimulus, was followed 0.5 seconds later by an identical auditory stimulus, referred to as the test stimulus. The length of time between stimulus pairs was 15 seconds. Inter-pair intervals are generally reported to be 10-15 seconds, a range that minimizes a potential influence from the previous stimulus pair (Adler L E, et al. (1986) Biol Psychiatry 21:787-798; Connolly P M, et al. (2003) Brain Res 992(1): 85-95; Stevens K E, et al. (1995) Psychopharmacology 119:163-170). The volume of auditory stimuli inside the recording chamber was 65 dB, which was 5 dB above the constant 60-dB background noise of the recording chambers. No startle response was evoked by this relatively low-level stimulation. Data acquisition software (SciWorks, Datawave Technologies, Berthoud, Colo., USA) digitized the EEG signals at 1,000 Hz, and was set to acquire 1 second of data starting 100 ms before, and ending 900 ms after, the initial conditioning stimulus. The software averaged the 120 paired responses into one composite evoked response. The measurement of hippocampal EP amplitudes was entirely computer automated using peak-finding analysis software (SciWorks). The EP response to auditory stimuli was identified as a peak deflection at a latency of 10-25 ms after the stimulus, followed by a peak of opposite polarity at 25-50 ms after the stimulus. The difference in amplitude between these two peaks was defined as the N40 amplitude in microvolts ($\mu V$). The mouse N40 amplitude, analogous to the human P50, was determined for both the averaged conditioning (CAMP) and test (TAMP) EPs and a ratio was derived between the two responses by dividing the test amplitude by the conditioning amplitude. This calculation, termed the T:C (test:conditioned) ratio, was the measure by which treatments were assessed for effects on sensory gating. T:C ratios were determined in each mouse for all recording sessions. DBA/2 mice with control T:C ratios below 0.60, and therefore lacking a sensory gating deficit, were excluded from the data analysis.

Drugs were administered 5 minutes before mice were placed into the recording chambers and the initiation of auditory EP recording. Recording of EPs continued for 30 minutes after the recordings began. For every experiment, each mouse was administered all treatments, including a vehicle control, on separate days, with at least 72 hours between treatments. This within-subjects design allowed each mouse to serve as its own control. The treatment order was randomized for each animal in all experiments.

Example 20 was dissolved using a vehicle combination of 5% dimethyl sulfoxide, 5% Solutol-HS15 (BASF), and 90% phosphate buffered saline (Sigma Chemical). Percentages are of the final solution volume.

The statistical analysis utilized for the dose response was a repeated measures ANOVA followed by a Newman-Keuls multiple comparison post hoc test to identify significant doses.

Figure 4:
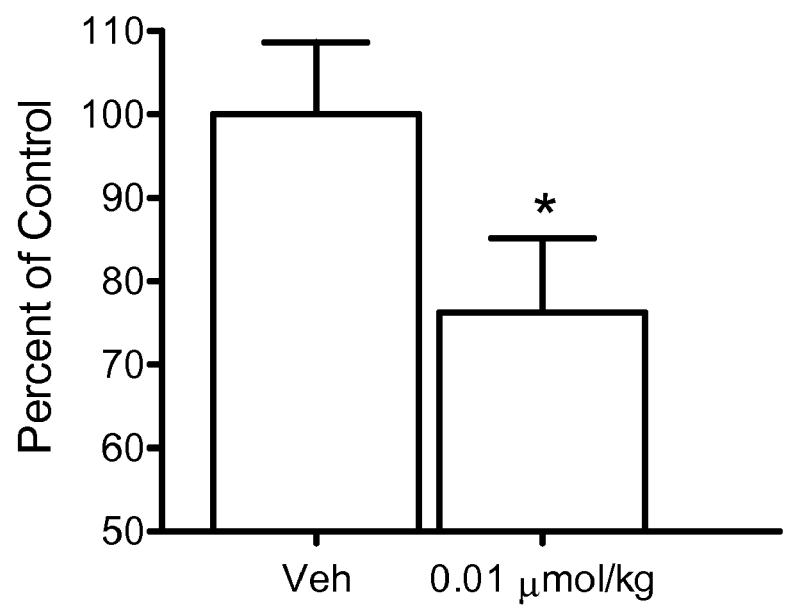
FIG. 4 is a graphical representation of the effect of vehicle or a PAM (Example 20) on sensory gating T:C (test:conditioned) ratios. A dose of 0.01 μmol/kg reduced T:C ratios by 23.7±8.9%. This effect to improve sensory gating by a PAM (Example 20) is indicative that schizophrenic patients could focus on relevant sensory stimuli, and ignore background noise.

The T:C ratio is an index of evoked potential suppression; a high ratio indicating little suppression, a low ratio greater suppression. Thus, reduction of T:C ratios by an agent would be considered a therapeutic improvement of sensory gating. FIG. 4 shows that a PAM (Example 20) at a dose of 0.01 $\mu$mol/kg lowers T:C ratios in DBA/2 mice by 23.7±8.9% when compared to vehicle. Therefore, positive allosteric modulation of $\alpha7$ neuronal nicotinic receptors by a PAM (Example 20) has the ability to improve sensory gating. This suggests that a PAM (Example 20) could improve the ability of schizophrenic patients to focus on relevant sensory stimuli, and not be distracted extraneous noise.

(vi) Sigma Receptor Binding Assay

The compounds of the invention are PAMs of $\alpha$-7 NNR, but not inhibitors of sigma receptors or do not show any significant binding to sigma receptors (for examples of sigma receptors ligands and their use, see for example, U.S. Pat. No. 6,057,371).

Sigma receptors are binding sites that interact with several psychoactive agents. Inhibition of specific binding of known ligands to sigma receptors ($\sigma1$ and $\sigma2$) was used to determine the selectivity of test compounds. The assays were performed as described previously in the literature (non-selective $\sigma$: Shirayama, Y., et al. Eur. J. Pharmacol. (1993), 237: 117-126. $\sigma1$: Ganaphthy, M. E., et al. *J. Pharmacol. Exp. Ther.* (1999) 289: 251-260. $\sigma2$: Bowen, M. D., et al. *Mol. Neuropharmacol.* (1993) 3: 117-126). The origin of the non-selective $\sigma$ receptors was rat cerebral cortex. The origin of the $\sigma1$ and $\sigma2$ receptors were Jurkat cells and rat cerebral cortex, respectively.

Affinity for the receptors was determined by competitive displacement of specific ligands (8 nM of [$^3$H]1,3-di(2-tolyl)guanidine for non-selective $\sigma$, 8 nM of [$^3$H](+)pentazocine for $\sigma1$ and 5 nM of [$^3$H]1,3-di(2-tolyl)guanidine for $\sigma2$) by test compounds. Nonspecific binding was determined by addition of an excess of an unlabelled binder (10 $\mu$M haloperidol).

The results are expressed as a percent inhibition of control specific binding (100−((measured specific binding/control specific binding)×100)) obtained in the presence of test compound (10 $\mu$M) as shown in Table 1. In addition, Table 1 includes data for the selected compounds from the voltage-clamp in *Xenopus laevis* oocytes assay.

TABLE 1

Sigma Receptor Inhibition and Activity in the Voltage-Clamp in *Xenopus laevis* Oocytes Assay

| Example Number | % Inhibition of Binding at 10 μM | | | Voltage-Clamp in *Xenopus laevis* Oocytes EC$_{50}$ (μM), (% max) |
|---|---|---|---|---|
| | σ | σ1 | σ2 | |
| 17 | | 8 | −1 | 0.18 (94%) |
| 22 | | 21 | −4 | 1.2 (115%) |
| 43 | | 84 | 34 | >10 (2%) |
| 19 | 6 | | | 5.4 (120%) |
| 20 | 39 | | | 0.097 (99%) |

Compounds of the invention are PAMs of $\alpha7$ NNR that can enhance the effects of a naturally occurring neurotransmitter, acetylcholine, or exogenously administered agonist. Although not being limited by theory, PAMs generally amplify agonist (acetylcholine) responses by (i) attenuating receptor desensitization so that the receptor remains open for longer duration and/or (ii) by directly amplifying the efficacy of ACh by enhancing maximal receptor activation. In either case, such compounds typically boost endogenous transmission of acetylcholine, and can do so in a temporally and spatially restricted manner since these effects will be localized to regions where the α7 receptors are expressed. Allosteric modulator compounds can modulate the function of α7 NNRs by enhancing ion channel function as measured by calcium responses described herein, or other approaches such as current or membrane potential studies.

In an embodiment, the compounds behave as PAMs in these assays between a concentration range of about 0.1 nM to about 10 μM. Allosteric modulation of the α7 NNR can trigger key signaling processes that are important to effects on memory, cytoprotection, gene transcription and disease modification. Therefore, the administration of a therapeutically effective amount of a compound of formula (I) to a mammal provides a method of selectively modulating the effects of α7 NNRs.

It is understood that the foregoing detailed description and examples are merely illustrative and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. Such modifications are intended to fall within the scope of the appended claims.

All references cited herein are hereby incorporated herein by reference in their entireties.

What is claimed is:

1. A method of treating a disorder or condition selected from the group consisting of acute pain, post-surgical pain, inflammatory pain, and neuropathic pain, comprising administering a therapeutically effective amount of a compound of formula (I):

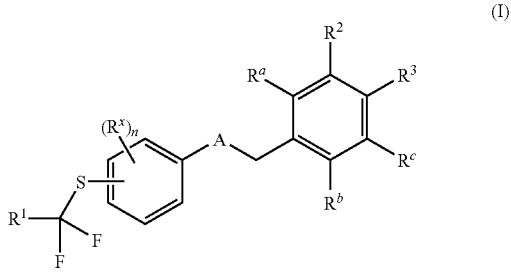

wherein,
A is —C(O)NH—;
$R^a$, $R^b$, and are independently hydrogen, alkenyl, alkoxy, alkoxycarbonyl, alkyl, alkylcarbonyl, alkylsulfonyl, alkylthio, cyano, haloalkoxy, haloalkyl, or halogen;

$R^x$ at each occurrence is independently acyloxy, alkoxy, alkyl, haloalkyl, halogen, or hydroxy;
n is 0, 1, 2, 3, or 4;
$R^1$ is hydrogen or halogen;
$R^2$ and $R^3$ are independently hydrogen, alkenyl, alkoxy, alkoxycarbonyl, alkyl, alkylcarbonyl, alkylsulfonyl, alkylthio, cyano, haloalkoxy, haloalkyl, halogen or $NR^5R^6$, provided that at least one of $R^2$ or $R^3$ is $NR^5R^6$;
$R^5$ and $R^6$ are independently hydrogen, alkenyl, alkoxyalkyl, alkoxycarbonyl, alkyl, alkylcarbonyl, alkylsulfonyl, arylalkyl, cycloalkyl, cycloalkylalkyl, haloalkyl, heteroarylalkyl, heterocycle, or heterocyclealkyl;
or a pharmaceutically acceptable salt, ester, or amide thereof.

2. The method of claim 1, further comprising administering in combination with atypical antipsychotics, cholinesterase inhibitors, histamine M3 antagonists, $5HT2_c$ antagonists, 5HT-6 antagonists, dopamine D1 agonists, muscarinic receptor antagonists, potassium channel blockers, α7 NNR ligands, or α4β2 NNR ligands.

3. The method of claim 1, wherein $R^1$ is hydrogen or fluorine.

4. The method of claim 1, wherein $R^5$ and $R^6$ are independently selected from hydrogen, alkyl, alkoxycarbonyl, alkylcarbonyl, alkylsulfonyl, arylalkyl, cycloalkyl, cycloalkylalkyl, haloalkyl, and heteroarylalkyl.

5. The method of claim 1, wherein the compound is selected from the group consisting of:
N-[4-(acetylamino)benzyl]-4-[(trifluoromethyl)thio]benzamide;
N-[4-(diethylamino)benzyl]-4-[(trifluoromethyl)thio]benzamide;
N-{3-[(methylsulfonyl)amino]benzyl}-4-[(trifluoromethyl)thio]benzamide;
N-[3-(methylamino)benzyl]-4-[(trifluoromethyl)thio]benzamide;
N-{4-[(methylsulfonyl)amino]benzyl}-4-[(trifluoromethyl)thio]benzamide;
N-[3-(dimethylamino)benzyl]-4-[(trifluoromethyl)thio]benzamide;
N-{3-[acetyl(methyl)amino]benzyl}-4-[(trifluoromethyl)thio]benzamide;
N-[4-(dimethylamino)benzyl]-4-[(trifluoromethyl)thio]benzamide;
N-(4-aminobenzyl)-4-[(trifluoromethyl)thio]benzamide;
N-[4-(methylamino)benzyl]-4-[(trifluoromethyl)thio]benzamide;
4-[(difluoromethyhthio]-N-[4-(dimethylamino)benzyl]benzamide; and
4-[(difluoromethyhthio]-N-[4-(methylamino)benzyl]benzamide;
or a pharmaceutically acceptable salt thereof.

* * * * *